US008529589B2

(12) United States Patent
Cartledge et al.

(10) Patent No.: US 8,529,589 B2
(45) Date of Patent: Sep. 10, 2013

(54) IMPLANTABLE PURSE STRING SUTURE TENSIONING DEVICE

(75) Inventors: Richard G. Cartledge, Boca Raton, FL (US); John P. Cartledge, Boca Raton, FL (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 215 days.

(21) Appl. No.: 12/738,742

(22) PCT Filed: Oct. 20, 2008

(86) PCT No.: PCT/US2008/080522
§ 371 (c)(1),
(2), (4) Date: Aug. 5, 2010

(87) PCT Pub. No.: WO2009/052509
PCT Pub. Date: Apr. 23, 2009

(65) Prior Publication Data
US 2010/0305609 A1    Dec. 2, 2010

Related U.S. Application Data

(60) Provisional application No. 61/088,506, filed on Aug. 13, 2008, provisional application No. 60/980,927, filed on Oct. 18, 2007.

(51) Int. Cl.
*A61B 17/04* (2006.01)
(52) U.S. Cl.
USPC .......................................... 606/148; 606/232

(58) Field of Classification Search
USPC ................... 606/74, 103, 148, 151, 157, 158, 606/232
See application file for complete search history.

(56) References Cited

U.S. PATENT DOCUMENTS

| 5,531,699 | A | * | 7/1996 | Tomba et al. | 606/148 |
| 5,649,940 | A | * | 7/1997 | Hart et al. | 606/148 |
| 5,891,159 | A | | 4/1999 | Sherman et al. | |
| 5,911,728 | A | * | 6/1999 | Sepetka et al. | 606/151 |
| 6,159,234 | A | * | 12/2000 | Bonutti et al. | 606/232 |
| 7,175,660 | B2 | | 2/2007 | Cartledge et al. | |
| 7,270,671 | B2 | * | 9/2007 | Fuseri et al. | 606/148 |
| 7,297,150 | B2 | | 11/2007 | Cartledge et al. | |
| 7,455,690 | B2 | | 11/2008 | Cartledge et al. | |

(Continued)

FOREIGN PATENT DOCUMENTS

| JP | 3073964 U | 9/2000 |
| JP | 2004033748 A | 2/2004 |
| JP | 2005534441 A | 11/2005 |
| WO | 2007015884 A2 | 2/2007 |

OTHER PUBLICATIONS

U.S. Appl. No. 13/123,768.
Dec. 10, 2008 International Search Report.

*Primary Examiner* — Julian Woo
(74) *Attorney, Agent, or Firm* — Lerner, David, Littenberg, Krumholz & Mentlik, LLP

(57) ABSTRACT

An implantable purse string suture tensioning device is provided, such that a hemostatic seal can be maintained without further manual adjustment over a range of purse string circumferences, including that surrounding a minimally invasive device, or a control or guidewire, and after complete removal of objects within the purse string suture, wherein the device is sized and shaped for in-dwelling implantation in a patient.

39 Claims, 25 Drawing Sheets

(56) References Cited

U.S. PATENT DOCUMENTS

| | | | |
|---|---|---|---|
| 7,875,056 B2 * | 1/2011 | Jervis et al. | 606/232 |
| 2006/0106405 A1 | 5/2006 | Fann et al. | |
| 2006/0241748 A1 | 10/2006 | Lee et al. | |
| 2007/0016287 A1 | 1/2007 | Cartledge et al. | |
| 2007/0299543 A1 | 12/2007 | Cartledge et al. | |
| 2008/0027483 A1 | 1/2008 | Cartledge et al. | |
| 2008/0109076 A1 | 5/2008 | Cartledge et al. | |
| 2008/0306586 A1 | 12/2008 | Cartledge et al. | |
| 2009/0125102 A1 | 5/2009 | Cartledge et al. | |
| 2009/0234404 A1 | 9/2009 | Fitzgerald et al. | |
| 2011/0009956 A1 | 1/2011 | Cartledge et al. | |
| 2011/0022168 A1 | 1/2011 | Cartledge | |
| 2011/0066231 A1 | 3/2011 | Cartledge et al. | |
| 2011/0093062 A1 | 4/2011 | Cartledge et al. | |
| 2011/0196480 A1 | 8/2011 | Cartledge | |
| 2011/0202130 A1 | 8/2011 | Cartledge et al. | |
| 2011/0208295 A1 | 8/2011 | Cartledge et al. | |
| 2011/0257633 A1 | 10/2011 | Cartledge et al. | |

* cited by examiner

# IMPLANTABLE PURSE STRING SUTURE TENSIONING DEVICE

CROSS-REFERENCE TO RELATED APPLICATIONS

The present application is a national phase entry under 35 U.S.C. §371 of International Application No. PCT/US08/80522 filed Oct. 20, 2008 which claims priority from U.S. Provisional Application No. 61/088,506, filed on Aug. 13, 2008, which further claims priority from U.S. Provisional Application No. 60/980,927, filed on Oct. 18, 2007, the disclosures of which are hereby incorporated by reference herein.

FIELD OF THE INVENTION

The present invention relates generally to the closure of surgical incisions, and more particularly to devices and methods for tensioning a purse string suture around and upon removal of a temporarily inserted elongated medical device.

BACKGROUND OF THE INVENTION

Purse string sutures are used to obtain hemostasis during a variety of surgical procedures. One example is during heart surgery, in which heart tissue is cannulated. A purse string suture is placed in the tissue prior to insertion of a cannula through the suture. The purse string suture is used both to limit bleeding during insertion and to create a hemostatic seal around the cannula after insertion and throughout the procedure.

One procedure in particular in which purse string sutures are used is mitral valve repair. Mitral valve repair can be performed by implanting an adjustable annular implant in the faulty mitral valve, as described in U.S. Pat. No. 7,175,660, incorporated herein by reference. The implant is adjusted for a period following the implantation, to obtain optimal effect. The adjustment is controlled by a detachable adjustment mechanism that may remain extending through the patient's atrium and chest upon closure of the incisions at the end of the implantation procedure. During the post-operative adjustment period, a hemostatic seal must be maintained around the adjustment tool. After the adjustment period, when the tool is detached from the implant and removed from the patient, it may be necessary to re-open the patient's chest to gain access to the atrium to re-establish hemostasis upon removal of the tool. For such a procedure, it would be desirable to provide a device that can be implanted to maintain the seal of a purse string suture around the catheter or adjustment tool during the adjustment period and to tighten the suture to obtain hemostasis when the catheter is removed without the need for further surgical intervention to close the internal incision.

Traditionally, purse string sutures have been tightened using a device such as a choker sleeve, or Romel tourniquet. With such a device, the ends of the suture are threaded through a small sheath and gripped with forceps on the side opposite the suture. The suture ends are then pulled using the forceps while the sleeve is pushed toward the suture loop, until the suture is adequately tight. Alternatively, the suture ends can be wrapped around the sheath, and the sheath then twisted, to tighten the suture. To keep a purse string suture tight around a cannula, for example, the sheath can be taped or otherwise held in place following tightening.

Other types of devices have been developed as alternatives to Romel tourniquets for tightening a purse string suture. One alternative, which can be used during minimally invasive surgery, is a knot-pusher. To use a knot-pusher, after stitching a purse string suture, the ends are tied in a half knot. The half knot is then pushed by the knot pusher toward the suture loop until the suture is adequately tight. For minimally invasive surgery, the knot-pusher can be long and slender for use through a trocar.

U.S. Pat. No. 5,911,728 discloses a purse string suture clamping device for use outside the body, which maintains tightness around a cannula or catheter while in a tissue structure. The clamping device includes a spring through which the ends of the suture extend, and a clamping means secured to the spring on the side opposite the suture. The suture ends are clamped while the spring means is compressed, and the spring then applies a constant tension to maintain a seal around the cannula.

These examples and other purse string suture tightening devices have deficiencies. First, the Romel tourniquet requires direct access to the site being sutured. Further, the tourniquet can not adjust to maintain tension if the suture becomes at all slack. While the knot-pusher requires only minimal access to the site, it does not allow for maintaining tightness after closure of the surgical incision. The knot-pusher also can not adjust to slack in the suture. The purse string suture clamping device is designed for external use with a cannula, not including removal of the cannula, and it is not capable of being implanted.

Therefore, it would be advantageous to provide a new and improved purse string tensioning device that is implantable, and is capable of maintaining the seal of a purse string suture around an elongated medical device and upon removal of the device.

SUMMARY OF THE INVENTION

An implantable purse string suture tensioning device and methods of use are provided, such that a hemostatic seal can be maintained without further manual adjustment over a range of purse string circumferences, including that surrounding a minimally invasive device, or a control or guidewire, and after complete removal of objects within the purse string suture, wherein the device is sized and shaped for in-dwelling implantation in a patient.

One object of the present invention is to provide devices and methods which enable a continuous seal of a purse string suture around an elongated medical device during a surgical procedure. The invention also provides devices and methods which enable a continuous seal of a purse string suture around an elongated medical device left in place following a surgical procedure. The invention also provides devices and methods which enable the automatic tensioning and continuous seal of a purse string suture upon removal of a medical device from the center of an incision.

The invention thereby provides devices and methods which enable the removal of a temporarily inserted medical device and dynamically provide the necessary purse string tensioning without re-opening the patient to access the tissue and manually re-tension the purse string suture. Another object of the present invention is to provide a device capable of sealing a purse string suture through a range of tension required for a variety of medical instruments or without an instrument inserted into the purse string suture. These and many other advantages and features of the invention will become apparent to those skilled in the art upon reading the present specification of the preferred embodiments.

In one aspect, the device includes at least one compressible tensioning element, which has a proximal end and a distal end. The device also includes a suture guide element, which has a proximal surface and a distal surface which is placed adjacent the exiting purse string sutures, and at least one passage therethrough for receiving a purse string suture. The device further may include at least one suture retaining element adapted to secure at least one end of a purse string suture proximal to the tensioning element. The suture guide element stabilizes the suture adjacent to the tensioning element, in a variety of configurations, so that the tensioning element can absorb excess suture length under a pre-determined pressure load throughout changes in the purse string length, as necessary to maintain hemostasis. The device is sized and shaped for in-dwelling implantation in a patient.

In one embodiment of the device, the passage through the guide element is linear. In another embodiment, the passage through the guide element is non-linear. In another embodiment, the suture enters the passage through the guide element substantially perpendicular to the plane of the tissue and exits the passage substantially parallel to the plane of the tissue. In a further embodiment, the guide element has a plurality of passages for receiving different ends of a suture.

In one embodiment, the tensioning element is secured in a compressed configuration by a removable tension retaining element prior to use of the purse string suture tensioning device. In one embodiment, removal of the tension retaining element allows the tensioning element to uncompress. In a particular embodiment, the tension retaining element is a c-clip or similar removable clamp. In another embodiment, the tension retaining element is a pin. In a further embodiment, the tension retaining element is a resorbable suture.

The tensioning device can also have a plurality of suture retaining elements. In one embodiment, the suture retaining element comprises a septum element, around the proximal end of which the ends of a suture can be tied. In one embodiment, the suture retaining element is located at the proximal end of the guide element. In one embodiment, the suture retaining element is attached to the tensioning element. In one embodiment, each suture retaining element corresponds to one end of a purse string suture. In a further embodiment, each suture retaining element corresponds to one tensioning element. The suture retaining element(s) can be attached to the corresponding tensioning element(s).

In a preferred embodiment, the guide element comprises two telescoping elements which permit a variable length for the suture passing therethrough, under the control of the tensioning element. In a preferred embodiment, at least a portion of the guide element extends through the tensioning element. In another embodiment, at least a portion of the tensioning element extends through or around the guide element. In one embodiment, the guide element is attached to the distal end of the tensioning element. In one embodiment, the proximal end of the guide element contacts the distal end of the tensioning element to prevent passage of the tensioning element therethrough in a preferred embodiment, the tensioning element is encased in all states of compression and expansion so as to prevent contact with the patient's body.

In another aspect, the device includes a guide element, which has a proximal and a distal end and at least one passage through it for receiving a purse string suture, and a compressible tensioning element, which has two lateral ends. Corresponding to each lateral end of the tensioning element, there is a passage element for distally receiving each respective end of a purse string suture. The suture ends are secured together proximal to the tensioning element. The device is sized and shaped for in-dwelling implantation in a patient.

Advantageously, the device can seal a purse string suture through a range of tension required with and without an elongated medical device inserted into the purse string suture.

In another aspect, a method is provided for internally sealing a purse string suture around an elongated medical device using an implantable purse string suture tensioning device. The method can comprise inserting at least one end of the purse string suture through the guide element, securing at least one end of the purse string suture proximal to the compressed tensioning element around at least one suture retaining element, and closing tissue over the device. The tensioning element is in a compressed configuration while the ends of the purse string suture are being secured. After the ends of the purse string suture have been secured, compression on the tensioning element is released to provide tension throughout the suture.

Alternatively, the method can comprise inserting both ends of a purse string suture through the guide element, threading each end of the purse string suture through a passage element, securing the ends of the suture together proximal to the tensioning element, and closing tissue over the device. The tensioning element is maintained in a compressed configuration while the ends of the suture are being secured, and thereafter the tensioning element is allowed to uncompress.

In one embodiment of the methods, the tissue is the heart. In one embodiment, the elongated medical device within the purse string suture is a cannula. In one embodiment, the tensioning element is secured in a compressed configuration by a tension retaining element prior to use of the tensioning device. In a further embodiment, removal of the tension retaining element allows the tensioning element to uncompress. In one embodiment, the tension retaining element is removed after the end(s) of the suture are secured around the suture retaining element(s).

BRIEF DESCRIPTION OF THE DRAWINGS

The objects and advantages of the present invention will be better understood and more readily apparent when considered in conjunction with the following detailed description and accompanying drawings which illustrate, by way of example, preferred embodiments of the purse string tensioning device and in which:

FIG. 1A shows a view of the purse string suture tensioning device in a compressed position, with a medical device extending through the suture. FIG. 1B shows a view of the purse string suture tensioning device in a partially uncompressed position, with a medical device extending through the suture. FIG. 1C shows a view of the purse string suture tensioning device in an uncompressed position, following removal of the medical device from the suture. FIG. 1D shows a cross-sectional view of the purse string suture tensioning device in an uncompressed position.

FIG. 2A shows a view of the purse string suture tensioning device in a compressed position, with a medical device extending through the suture. FIG. 2B shows a view of the purse string suture tensioning device in a partially uncompressed position, with a medical device extending through the suture. FIG. 2C shows a view of the purse string suture tensioning device in an uncompressed position, following removal of the medical device from the suture. FIG. 2D shows a cross-section view of the purse string suture tensioning device in an uncompressed position.

FIG. 3A shows a purse string suture tensioning device in a compressed position. FIG. 3B shows a purse string suture tensioning device in an uncompressed position.

FIG. 7A shows a view of the purse string suture tensioning device in a compressed position, with a medical device extending through the suture. FIG. 7B shows a view of the purse string suture tensioning device in a partially uncompressed position, with a medical device extending through the suture. FIG. 7C shows a view of the purse string suture tensioning device in an uncompressed position, following removal of the medical device from the suture.

FIG. 8 is a perspective view of an incision being made in tissue.

FIG. 9 is a perspective view of a purse string suture placed around the incision of FIG. 8.

FIG. 10 is a perspective view showing the purse string tensioning device of FIG. 1 placed adjacent to the incision with the tensioning element in a compressed configuration and the suture tied off.

FIG. 11 is a perspective view showing the purse string tensioning device of FIG. 1 placed adjacent to the incision with the tensioning element in a partially uncompressed configuration following removal of the tension retaining element.

FIG. 13A shows the embodiment in a relaxed configuration. FIG. 13B shows the device in a pre-compressed position, with a medical device extending through the suture. FIG. 13C shows the device after the tension retaining element has been removed, with a medical device extending through the suture. FIG. 13D shows the device in an uncompressed position, following removal of the medical device from the suture.

FIG. 14A is a perspective view showing the embodiment in a compressed configuration. FIG. 14B is a cross-sectional view showing the embodiment in a compressed configuration. FIG. 14C is a cross-sectional view showing the embodiment in an expanded configuration.

FIG. 15A is a perspective view showing the embodiment in an expanded configuration. FIG. 15B is a cross-sectional view showing the embodiment in an expanded configuration. FIG. 15C is a cross-sectional view showing the embodiment in a compressed configuration.

FIG. 16A is a perspective view showing the embodiment in a compressed configuration. FIG. 16B is another perspective view showing the embodiment in a compressed configuration. FIG. 16C is a perspective cross-sectional view showing the embodiment in a compressed configuration. FIG. 16D is a perspective cross-sectional view showing the embodiment in an expanded configuration. FIG. 16E is a perspective view showing the embodiment in an expanded configuration.

DETAILED DESCRIPTION OF THE PREFERRED EMBODIMENTS

Figure 1A:
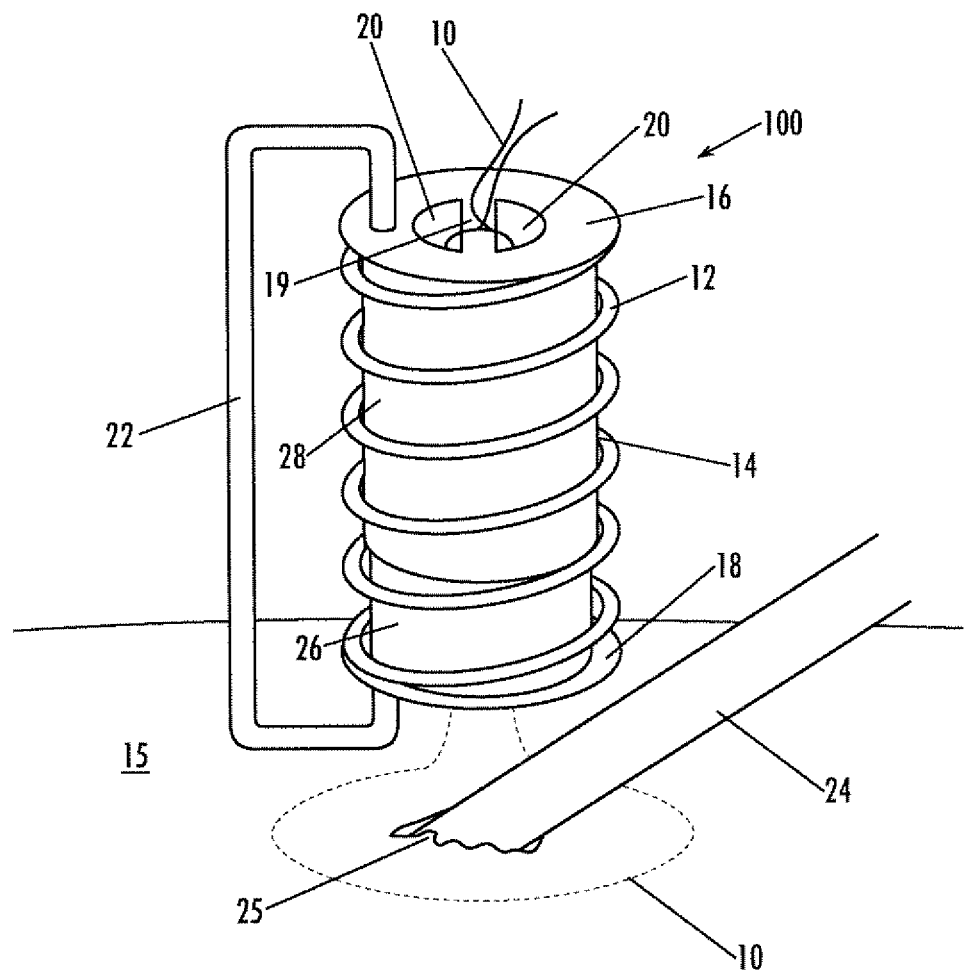
FIGS. 1A-D are schematic views of one embodiment of the purse string suture tensioning device.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Purse string sutures are well known in the art and are used primarily to obtain hemostasis and prevent blood loss. A purse string suture is placed by running a continuous stitch through the target tissue in a circular pattern. When used in conjunction with a medical device, the diameter of the purse string suture is chosen according to the diameter of the device to be inserted through the suture. One end of the suture thread remains outside of the tissue while the stitch is placed using a needle, and the other end is pulled back outside of the tissue after the circular stitch is completed. The suture needle may then be cut from the suture thread.

Before insertion of an elongated medical instrument though the center of the suture, the suture is tensioned by pulling the trailing ends taut. Once the instrument has been inserted, the ends are again pulled taut to form a hemostatic seal around the instrument. A seal must be maintained around the instrument as long as it remains in the tissue. Upon removal of the instrument from the tissue, the suture must again be tightened to create a seal without the instrument.

An improved purse string suture tensioning device has been developed for use in maintaining a seal around a minimally invasive elongated medical device such as a cannula or catheter, and further hemostatic sealing of tissues upon removal of the elongated medical device. The purse string suture tensioning device is, therefore, implantable and provides a means for maintaining a seal around a temporarily inserted medical device, and is self-adjusting to obtain hemostasis upon removal of the medical device. Advantageously, the tensioning device can adjust to slack in the suture to keep the suture tight while the elongated medical device is in the patient. Further, the tensioning device allows for taking up additional suture slack upon removal of the medical device without having to re-open the patient.

In one aspect of the present invention, the purse string suture tensioning device includes at least one compressible tensioning element, which has a proximal end and a distal end. The device also includes a guide element, which has a proximal surface and a distal surface and at least one passage therethrough, for receiving a purse string suture. The device may further include at least one suture retaining element adapted to secure at least one end of a purse string suture proximal to the tensioning element. The guide element operates to stabilize the suture adjacent to the tensioning element, such that the tensioning element absorbs excess suture length under a pre-determined pressure load throughout changes in the purse string length, as required to maintain hemostasis. The device is sized and shaped for in-dwelling implantation in a patient.

In various embodiments, the passage through the guide element is linear or non-linear. In a preferred embodiment, the suture enters the passage through the guide element substantially perpendicular to the plane of the tissue and exits the passage substantially parallel to the plane of the tissue. In other preferred embodiments, the guide element has two separate passages for receiving respective ends of the purse string suture.

The tensioning element can be any compressible form. The tensioning configuration can be coiled, hairpin, or any known such configuration imparting a biasing force. In a preferred embodiment, the tensioning element is a coiled spring. The length and compression strength of the tensioning element can vary, and should be chosen to suit the particular surgical application. The compression distance, or difference in length between the compressed and uncompressed positions of the tensioning element should be as long as necessary to absorb the slack generated in the suture upon removal of the medical instrument from the suture. This length depends upon the size of the surgical tools intended to be used within the purse string suture.

In certain embodiments of the tensioning device of the present invention, at least a portion of the guide element extends through the tensioning element. Alternatively, the guide element extends through at least a portion of the tensioning element. In further embodiments, at least a portion of the tensioning element extends through the guide element, or the tensioning element extends through at least a portion of the guide element.

The invention provides that in certain embodiments, the tensioning device is provided with a removable tension retaining element which retains the tensioning element in a compressed configuration. The tension retaining element can be, for example, a c-clip or similar clamp or a pin that retains compression on the tensioning element during surgical placement of the device, threading of the suture through the guide element, and securing of the purse string suture ends. To help keep track of the small part before and during surgery and for ease of removal from the body, the tension retaining element is preferably attached to a suture loop or other handle. Alternatively, the tension retaining element can be a resorbable suture.

The present invention provides various embodiments wherein the suture guide element further comprises a plurality of telescoping elements permitting variable length of the suture passing therethrough. For example, the invention provides that the guide element can further comprise proximal and distal guide elements, which can telescope within one another to extend or contract the length of the suture passage. In certain embodiments, the tensioning element is fully encased to prevent contact with the patient's body when the tensioning element is in any state or compression and expansion.

In certain embodiments, the invention further provides a suture retaining element for securing the purse string suture during or after the surgical procedure. The suture retaining element can be in the form of a tie-off cleat, cinch or other physical extension around which the suture ends can be wrapped and/or tied for temporary or permanent securing of the suture. In one embodiment, the suture retaining element is a proximal septum between separate passages within the guide element for each end of the purse string suture. The ends of the suture can be permanently tied-off proximal to the septum. In another embodiment, the suture retaining element comprises structures within the guide element around which the suture ends are wrapped and tied.

The present invention provides methods for sealing a purse string suture around an elongated medical device using the purse string suture tensioning devices described above, comprising: a) inserting at least one end of the purse string suture through the distal surface of the guide element; b) securing the at least one end of the purse string suture proximal to the tensioning element, wherein the tensioning element is in a compressed configuration while the at least one end of the purse string suture is being secured; c) releasing compression on the tensioning element to provide tension throughout the purse string; and c) closing tissue over the device. In preferred embodiments of the method, the tissue is a heart, particularly the atrial wall of a heart. In other preferred embodiments, the elongated medical device inserted within the purse string is a cannula, catheter, guidewire or control wire for post-operatively adjusting an implanted medical device, such as a prosthetic mitral valve.

Alternative embodiments of the device of the present invention include an implantable purse string suture tensioning device comprising a guide element having a proximal surface and a distal surface and at least one passage therethrough, for receiving a purse string suture; a tensioning element, having a first lateral end and a second lateral end; a plurality of passage elements, one attached to each end of the tensioning element, for receiving a respective end of the purse string suture; wherein the device is sized and shaped for in-dwelling implantation in a patient. In such embodiments, the tensioning element can be substantially parallel to the plane of the tissue. Furthermore, in such embodiments, the passage through the guide element can be linear or non-linear and there can be two separate passages for receiving separate ends of the purse string suture. This embodiment similarly provides a device that seals a purse string suture through a range of tension required with and without an elongated medical device inserted into the purse string suture.

The invention provides methods of using the above embodiments, comprising inserting the ends of the purse string suture through the guide element, threading each end of the purse string suture through a corresponding passage element; securing the ends of the suture together, wherein the tensioning element is in a compressed configuration while the ends of the suture are being secured; and closing tissue over the device.

The purse string suture tensioning device can be further understood with reference to the exemplary, non-limiting embodiments illustrated in FIGS. 1-16.

One embodiment of the purse string suture tensioning device is shown in FIGS. 1A-D. The tensioning device 100 includes a coiled spring tensioning element 12, which is disposed about a guide element 14 having a proximal surface 16 and a distal surface 18, adapted to be adjacent a patient's tissue 15. The guide element 14 has two separate passages 20 therethrough for receiving separate ends of the purse string suture 10. The guide element passages 20 are divided by a septum serving as a suture retaining element 19, which can be used to tie-off the ends of the purse string suture 10 proximal to the tensioning element 12. The purse string suture 10 (shown as stitches on the tissue 15) is surrounding a surgical instrument 24, such as a cannula, catheter, or control wire, which penetrates the tissue 15. The circumference of the purse string suture 10 in the tissue 15 must be greater than the circumference of the surgical instrument 24, to allow the instrument 24 to pass through the suture 10.

Figure 1B:
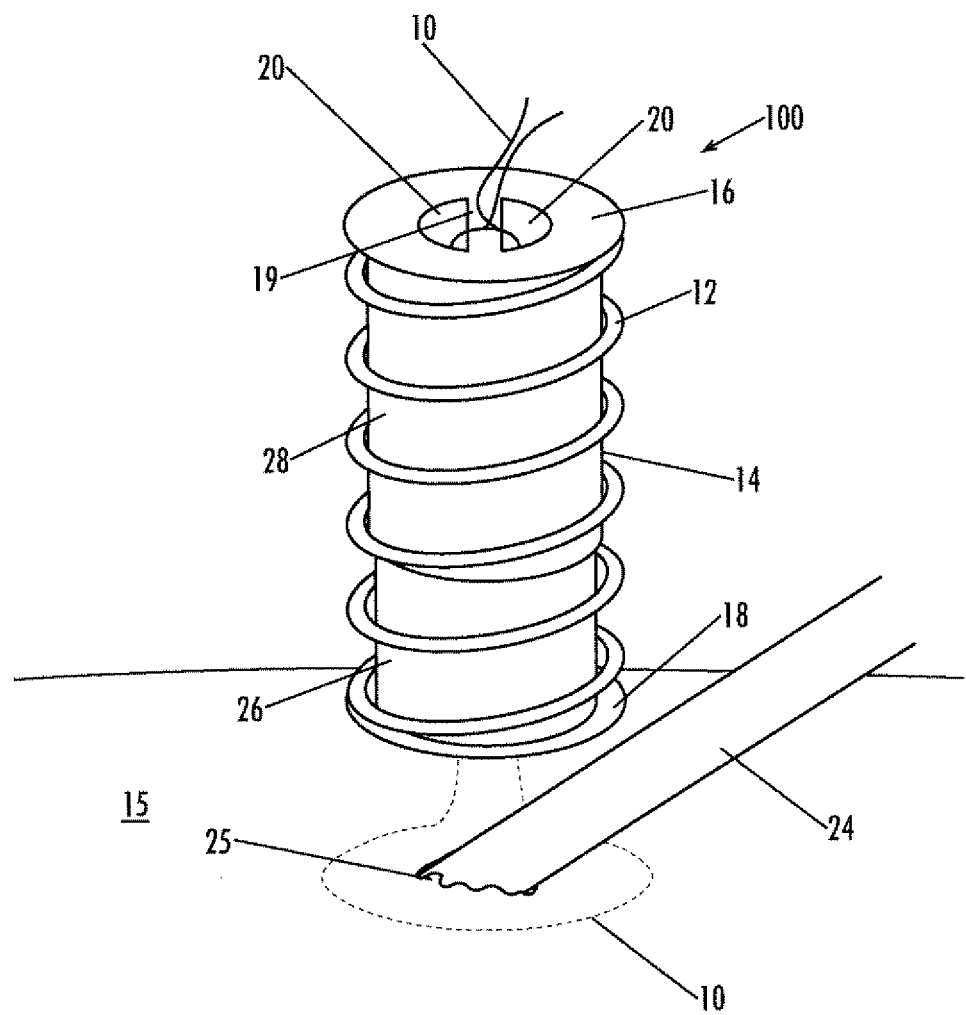

The device 100 in FIG. 1A is shown in a compressed position, maintained as such with a tension retaining element 22. The device 100 may be compressed prior to surgery or may be sold in a pre-compressed position, in which case the tension retaining element 22 is already in place. As mentioned previously, the tension retaining element 22 permits the placement of the device 100, including the threading of the ends of the suture 10 through the passages 20 in the guide element 14 and the tying of the suture ends, while no pressure is being exerted on the purse string suture 10. The tension retaining element 22 also eliminates the need for a person to compress the tensioning element 12 while the ends are being threaded through the passages 20 and secured together. After proper placement and securing of the ends of the suture 10, the tension retaining element 22 can then be removed, permitting the tensioning element 12 to expand, and thus take up any slack in the purse string suture 10, to a predetermined amount of tension so as to provide a hemostatic seal of an incision 25 around an instrument 24, such as a cannula, catheter, or control wire, as shown in FIG. 1B. Additionally, securing the ends when the tensioning element 12 is tightly compressed allows for maximal tension to be placed on the suture 10 when the tension retaining element 22 is removed and avoids damage to the suture 10 that could occur from securing the suture 10 under tensioning stress.

Figure 1C:
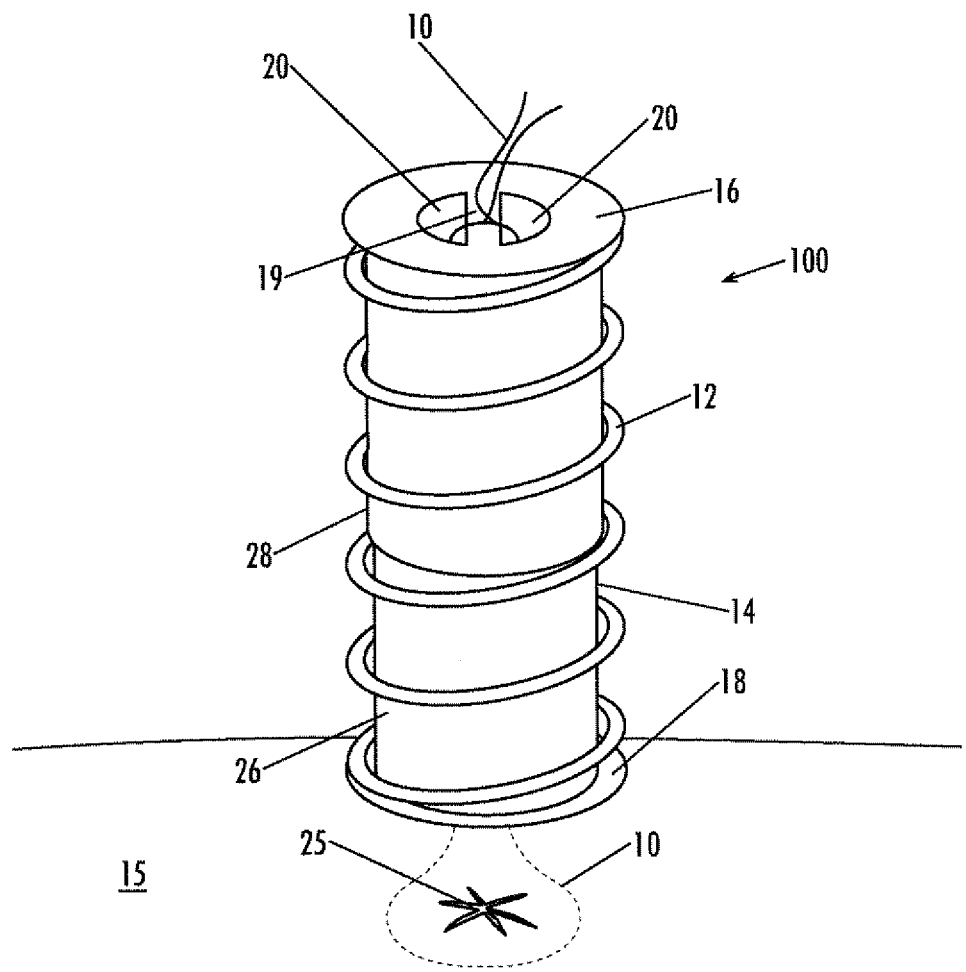

FIG. 1C shows the further expansion of the tensioning element 12 to take up slack in the suture 10 after withdrawal of the surgical instrument 24 from the incision 25, which will be described in more detail below.

Figure 1D:
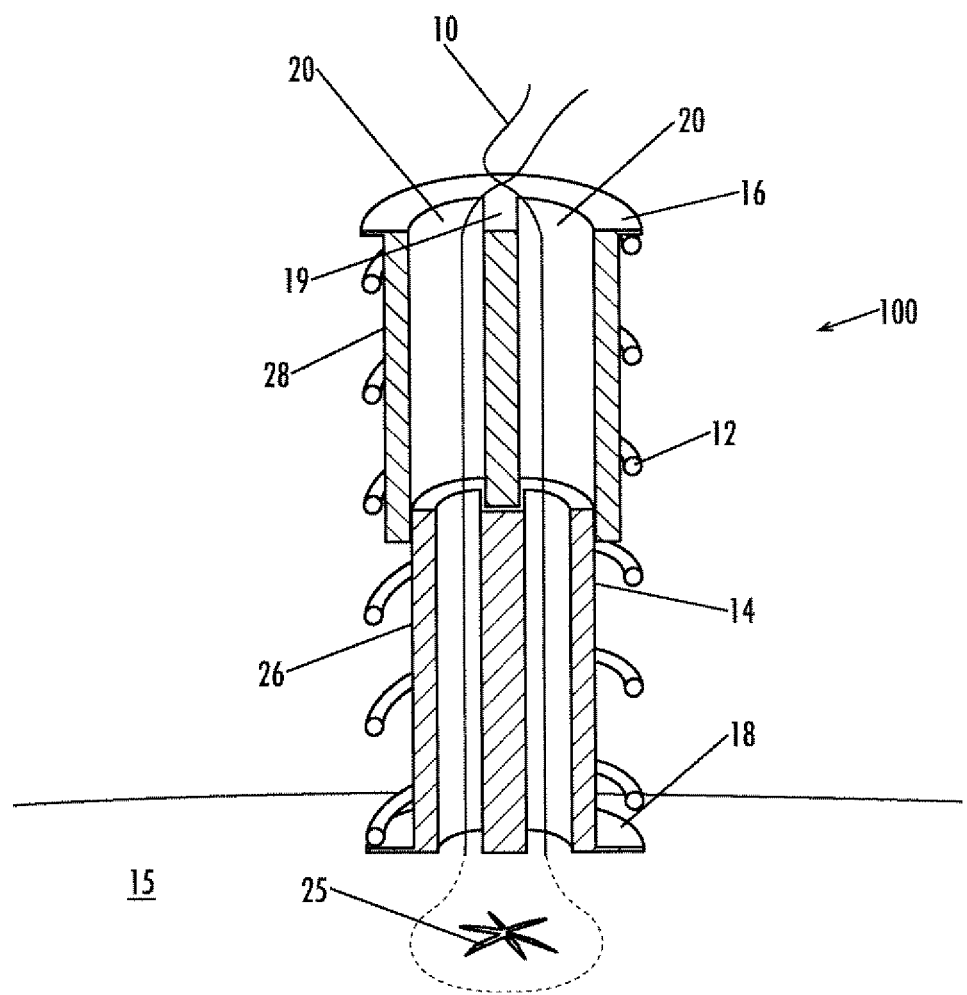

The size and compression distance, or difference in length between the compressed and expanded configurations, of the tensioning element 12 should be selected to be great enough to take up all slack in the suture 10 upon removal of the surgical instrument 24 from the incision 25. The required compression distance of the tensioning element 12 varies based on the circumference of the medical device 25 and, correspondingly, the suture 10, how many tensioning elements 12 there are taking up slack, and the amount of overlap in the suture the circumference of within the device 100. As shown in FIG. 1D, for example, there is one tensioning element 12 and the two ends of the suture 10 are being pulled equally within the guide element 14, so the compression distance of the tensioning element 12 needs to be at least half the length of the suture slack being absorbed. In preferred embodiments, the compression distance varies between 5 mm and 15 mm.

The amount of tension exerted by the tensioning element(s) should be selected to be great enough to obtain hemostasis. The tension required to obtain hemostasis may vary according to factors such as the surgical application and the age and condition of the patient's organ in which the suture is placed. In one embodiment, the desired amount of pressure may vary between 1 pound and 5 pounds. For applications involving a patient's heart, the desired amount of pressure may vary between 1.5 and 3.5 pounds, preferably between 2 and 3 pounds. The tensioning element(s) can be calibrated to exert the desired amount of tension.

As can be seen in FIGS. 1A-D, the guide element 14 of this embodiment is constructed of telescoping sections. The distal guide section 26 telescopes within the proximal guide section 28 for expansion and contraction based on the opposing forces on the purse string suture 10 of the tensioning element 12 versus the desired amount of hemostatic pressure required at the site of the incision 25. It will be appreciated that in alternative embodiments, the proximal guide section 26 could easily telescope within the distal guide section 28.

Furthermore, the shapes and dimensions of the guide element 14 and the passage 20 therethrough can vary widely. As shown in FIGS. 1A-D, the guide element may be cylindrical, but the guide element may also be an oval, a rectangle with rounded edges, or a variety of other shapes so long as the device is suitable for implantation within a patient. In any shape, the device preferably has smooth curves and rounded edges to minimize irritation within the patient's body. The passage through the guide element may be a single channel or two separate channels, as shown in the cross-sectional view in FIG. 1D, and additionally may be linear or non-linear, as exemplified below. In alternative embodiments discussed below, rather than having a separately encased passage within, the passage is the hollow channel of the guide element as a whole.

The orientation of the passage or passages with respect to the guide element can vary depending upon the preference for the particular application and anatomical obstructions or interferences. The passages 20 in the embodiment shown in FIGS. 1A-D are linear and are substantially perpendicular to the plane of the tissue 15 for their entire length. The passages 220 in the embodiment shown in FIGS. 2A-D each have two linear segments with a perpendicular bend, such that the ends of the suture 210 enter each passage 220 perpendicular to the plane of the tissue and exit the passage 220 parallel to the plane of the tissue 215. The orientation of the separate passages 220 is shown in the cross-sectional view in FIG. 2D.

The tensioning device 200 in FIGS. 2A-D includes a coiled spring tensioning element 212, which is disposed about a guide element 214 having a proximal surface 216 and a distal surface 218, adapted to be adjacent a patient's tissue 215. The guide element 214 has two separate passages 220 therethrough for receiving separate ends of the purse string suture 210. The guide element passages 220 are divided by a septum serving as a suture retaining element 219, which can be used to tie-off the ends of the suture 210 proximal to the tensioning element 212.

Figure 2A:
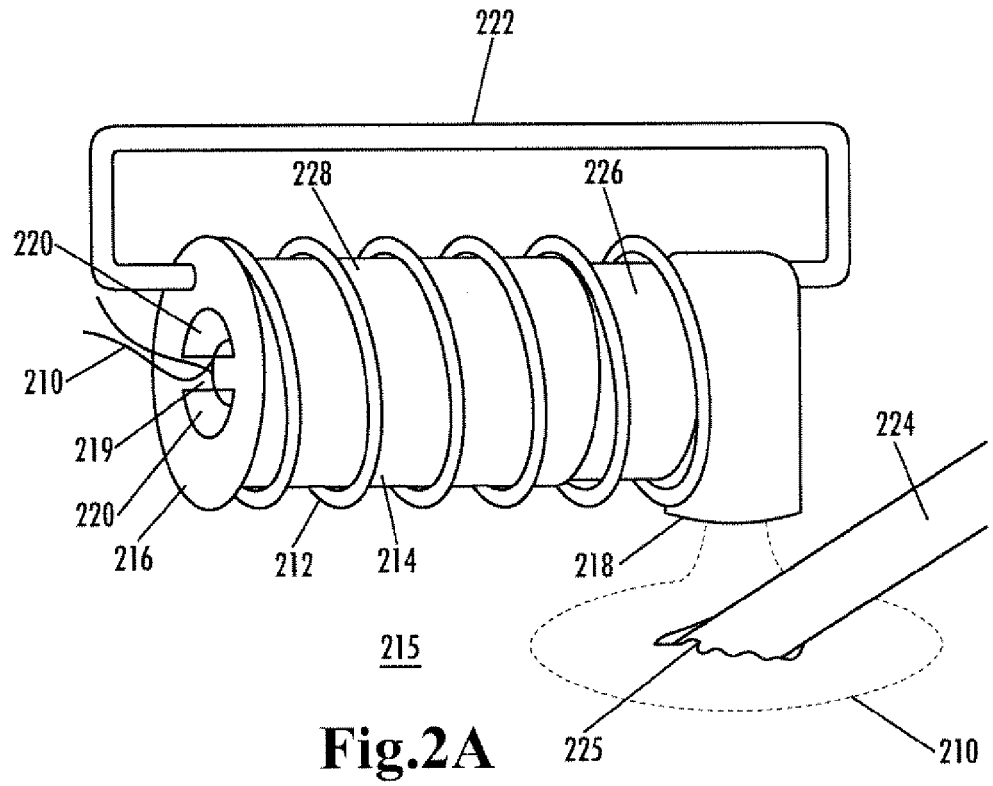
FIGS. 2A-D are schematic views of another embodiment of the purse string suture tensioning device.
Figure 2B:
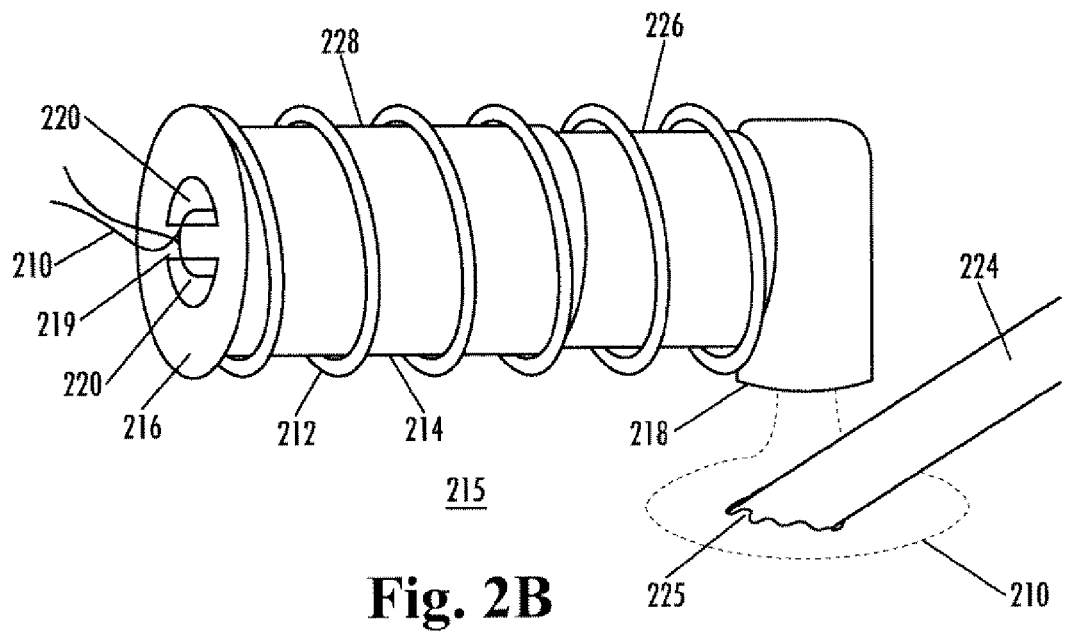
Figure 2C:
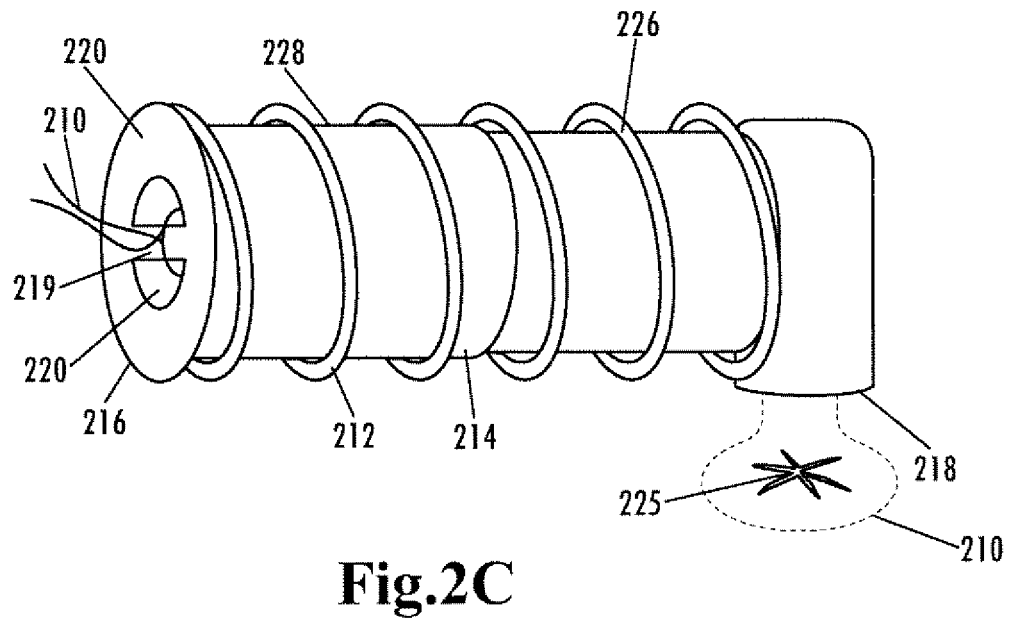
Figure 2D:
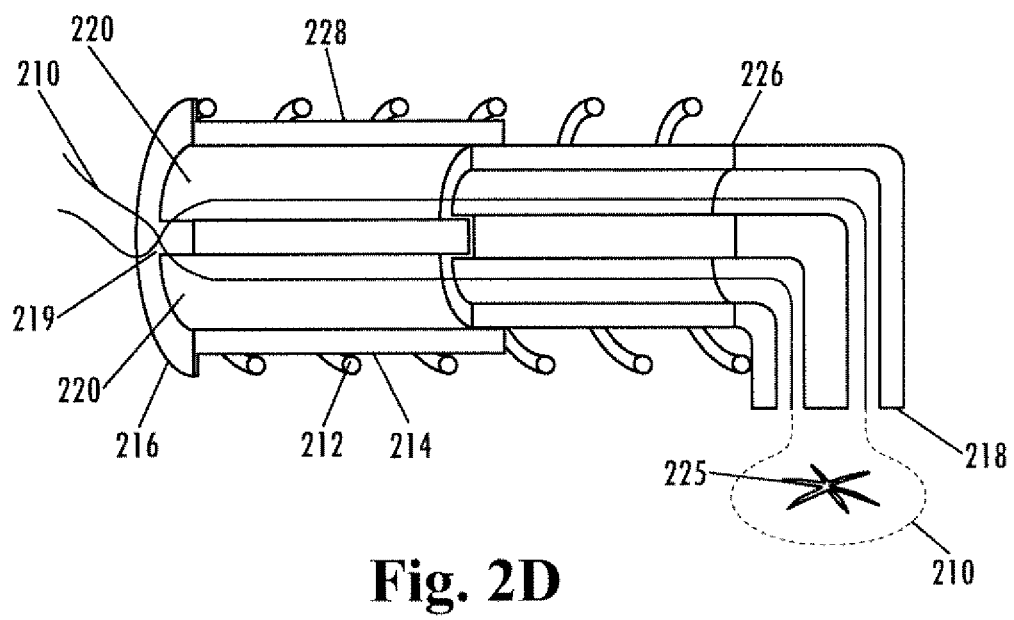

The device in FIG. 2A is shown in a compressed position, maintained as such with a tension retaining element 222. After proper placement and securing of the ends of the suture 210, the tension retaining element 222 can then be removed, permitting the tensioning element 212 to expand, and thus take up any slack in the purse string suture 210 during the surgical procedure, as shown in FIG. 2B. Upon withdrawal of the surgical instrument 224 from the incision 225, the tensioning element 212 expands further to take up the additional slack, as shown in FIG. 2C.

As can be seen in FIGS. 2A-D, the guide element 214 of this embodiment is constructed of telescoping sections. The distal guide section 226 telescopes within the proximal guide section 228 for expansion and contraction based on the opposing forces on the purse string suture 210 of the tensioning element 212 versus the desired size of the suture 210 and amount of hemostatic pressure required at the site of the incision 225. It will be appreciated that in alternative embodiments, the proximal guide section 228 could easily telescope within the distal guide section 226.

Figure 3A:
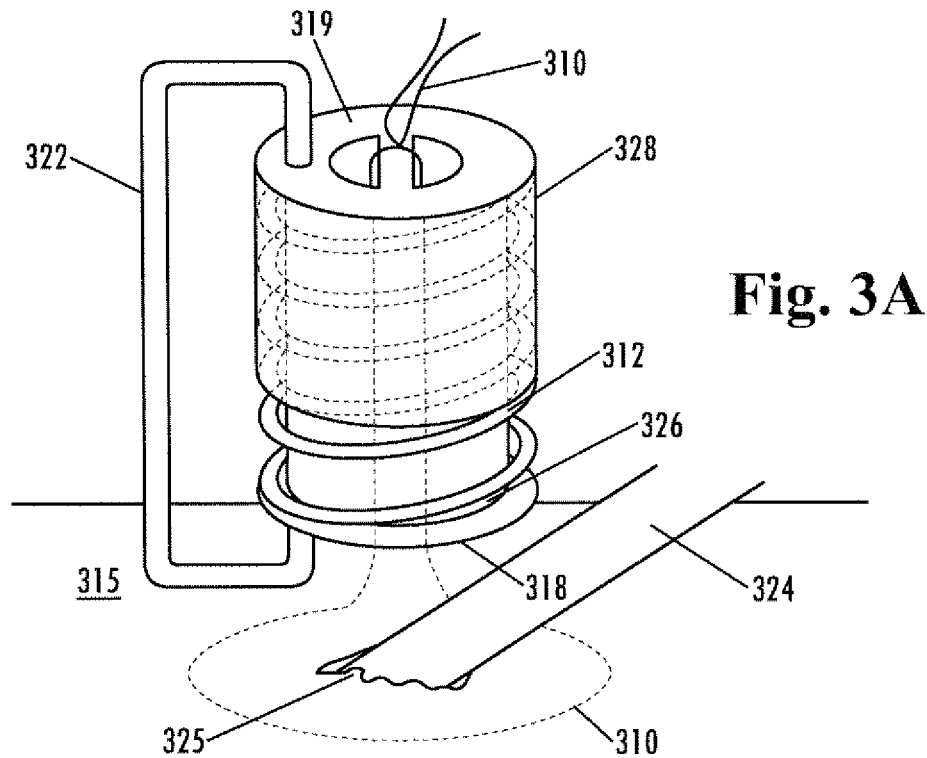
FIGS. 3A-B are schematic views of an alternate embodiment of the purse string suture tensioning device.
Figure 3B:
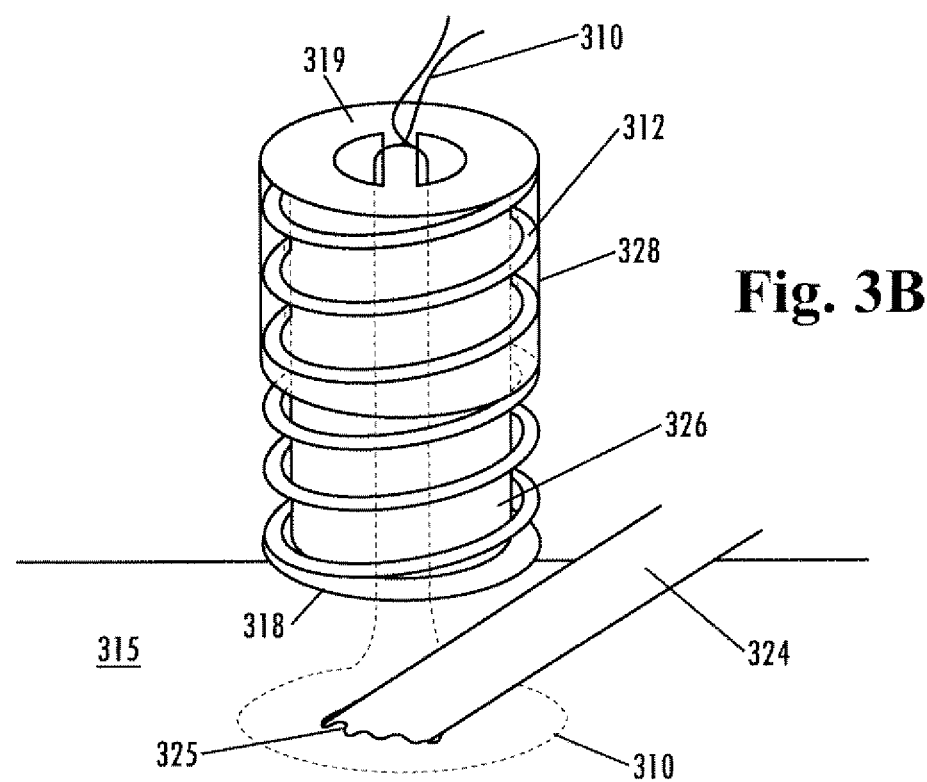
Figure 4:
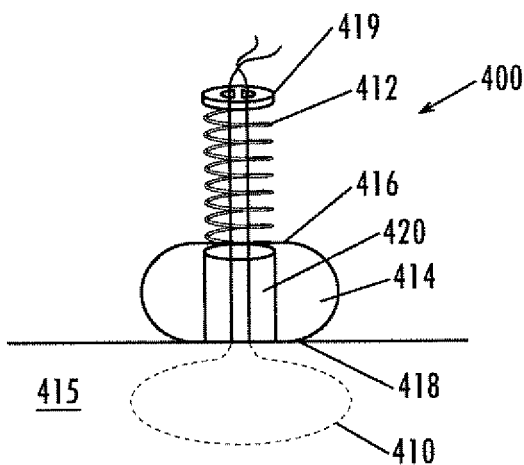
FIG. 4 is a schematic view of another embodiment of the purse string suture tensioning device.

FIGS. 3A and 3B show an alternative embodiment of the invention in varying states of compression. In this embodiment, the tensioning element 312 is disposed around the distal guide section 326 and within the proximal guide section 328. The proximal guide section 328 advantageously covers a portion of the tensioning element 312 to prevent contact with the patient's tissue. The distal surface 318 of the guide element 314 is shown adjacent the tissue 315, and the ends of the suture 310 are shown tied-off around a suture retaining element 319. In FIG. 3A, the embodiment is shown with the tensioning element 312 held in a compressed configuration by a tension retaining element 322, such that there is no tension placed on the purse string suture 310. In FIG. 3B, the telescoping sections 326, 328 are in a partially extended position, creating some tension in the suture 310 around the surgical instrument 324.

Figure 14A:
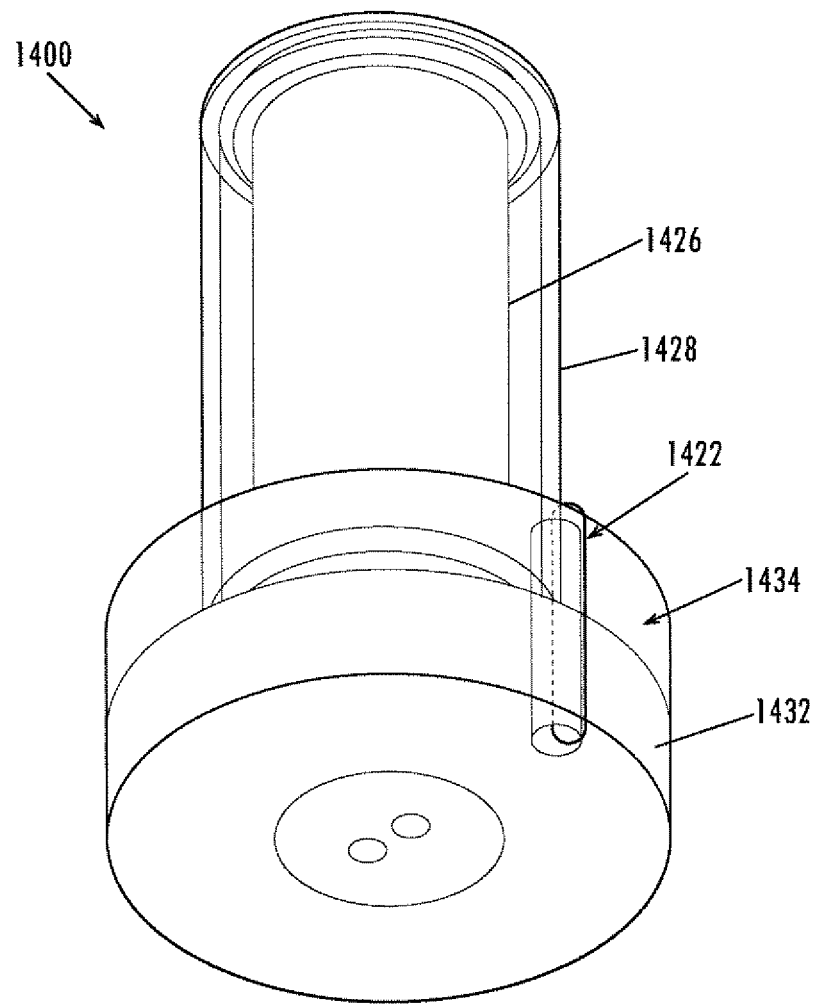
FIGS. 14A-C are views of an alternative embodiment of the purse string suture tensioning device.
Figure 14B:
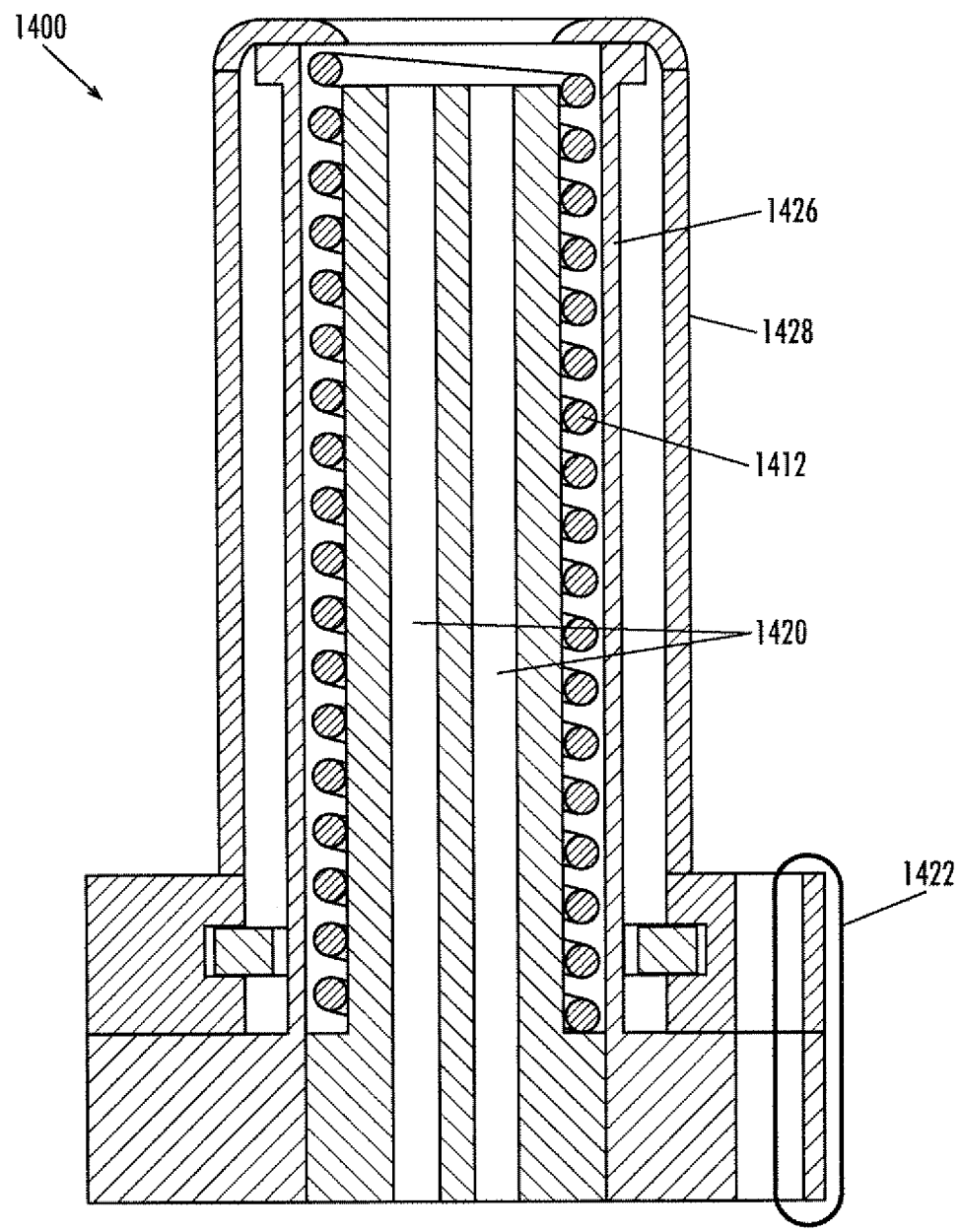
Figure 14C:
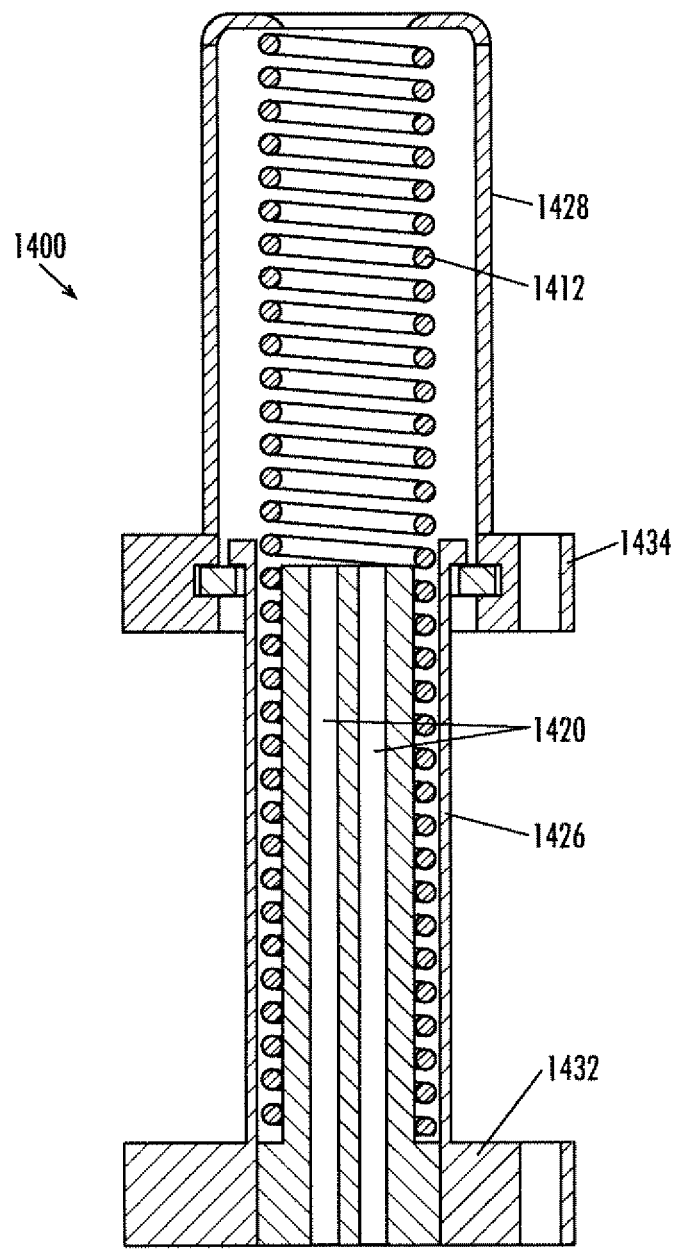

FIGS. 14A-C show another embodiment of the invention comprising telescoping sections. FIGS. 14A and 14B are different views of the embodiment in a compressed configuration. FIG. 14C shows the embodiment in an expanded configuration. Like some of the previously disclosed embodiments, this embodiment 1400 has a guide element that is constructed of telescoping sections. The distal guide section 1426 telescopes within the proximal guide section 1428. Each guide section has a rim at its distal end. The rim 1432 of the distal guide section 1426 is adjacent the tissue (not shown) and contains two openings which receive the ends of the purse string suture (not shown) and lead the ends through two separate passages 1420 (visible in FIGS. 14B and 14C) in the distal guide section 1426. The rim 1434 of the proximal guide section 1428 rests on the rim 1432 of the distal guide section 1426 when the tensioning element 1412 is fully compressed. The device 1400 can be held in this compressed position using a tension retaining element 1422. The tension retaining element 1422 may be a clip or clamp. In an alternative embodiment, the tension retaining element 1422 is a pin. The rim of either the distal or proximal guide section may have a projection which extends into a matching recess in the other rim, and the pin extends transversely through a hole in one rim and an aligned hole in the projection on the other rim to secure the two rims together until the pin is removed. In a preferred embodiment, the tension retaining element 1422 is a suture tied through aligned holes in the rims 1432, 1434 and then around the outer surface of the rims 1432, 1434, as shown in FIGS. 14A and 14B. Using a suture as a tension retaining element 1422, in place of a clip, clamp, or pin eliminates the need for this additional part during surgery and the potential risk of leaving the small part in the patient's body. The suture tension retaining element 1422 may be a resorbable material that does not cause any harm if it is left in the patient's body.

As in previous embodiments, there is a suture retaining element (not shown) at the proximal end of the tensioning element 1412. The suture retaining element can be a septum or any other means of securing the suture ends. When there is slack in the purse string suture, the tensioning element 1412 expands to take up the slack, and the telescoping sections 1426, 1428 slide apart, as shown in FIG. 14C. The purse string suture 1410 extends through the passages 1420 in the distal guide element 1426 and into the passage created by the hollow center of the tensioning element 1412. Alternatively, there may be a defined passage or passages within the center of the tensioning element 1412, as through the distal guide section 1426. In this embodiment, the tensioning element 1412 is fully encased by the distal guide section 1426 to avoid contact with the patient's body in all states of compression and expansion. Such encasing advantageously prevents irritation or pinching that could be caused by contact with the tensioning element 1412.

Figure 15A:
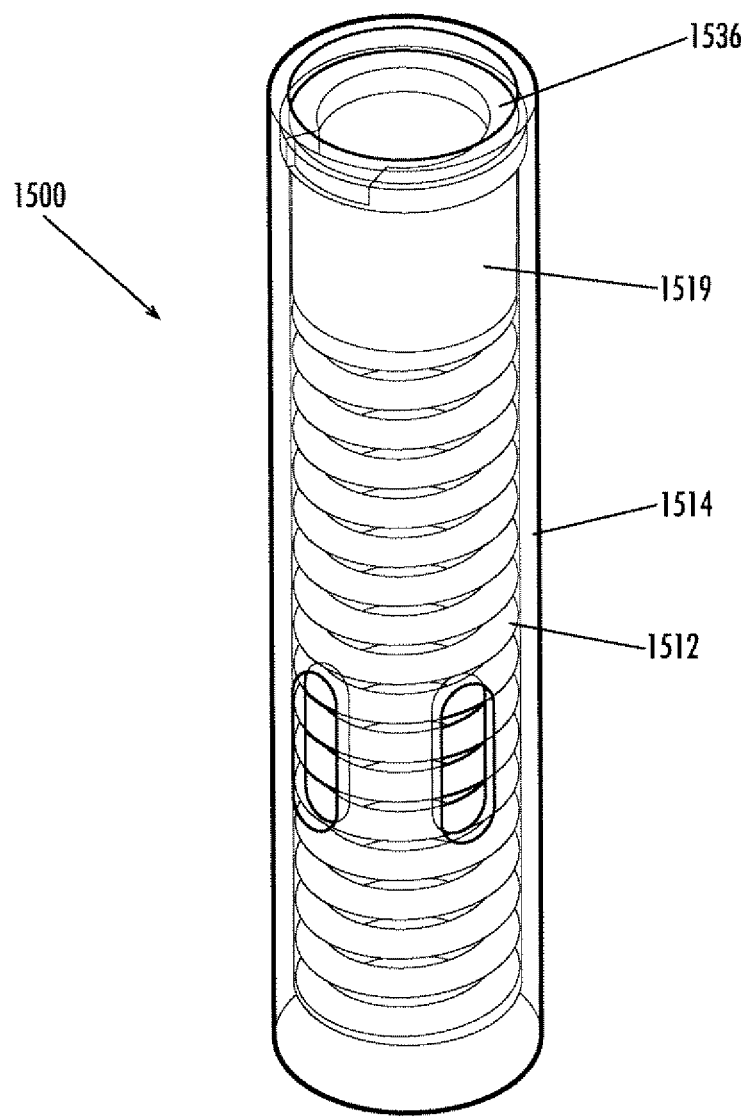
FIGS. 15A-C are views of an alternative embodiment of the purse string suture tensioning device.
Figure 15B:
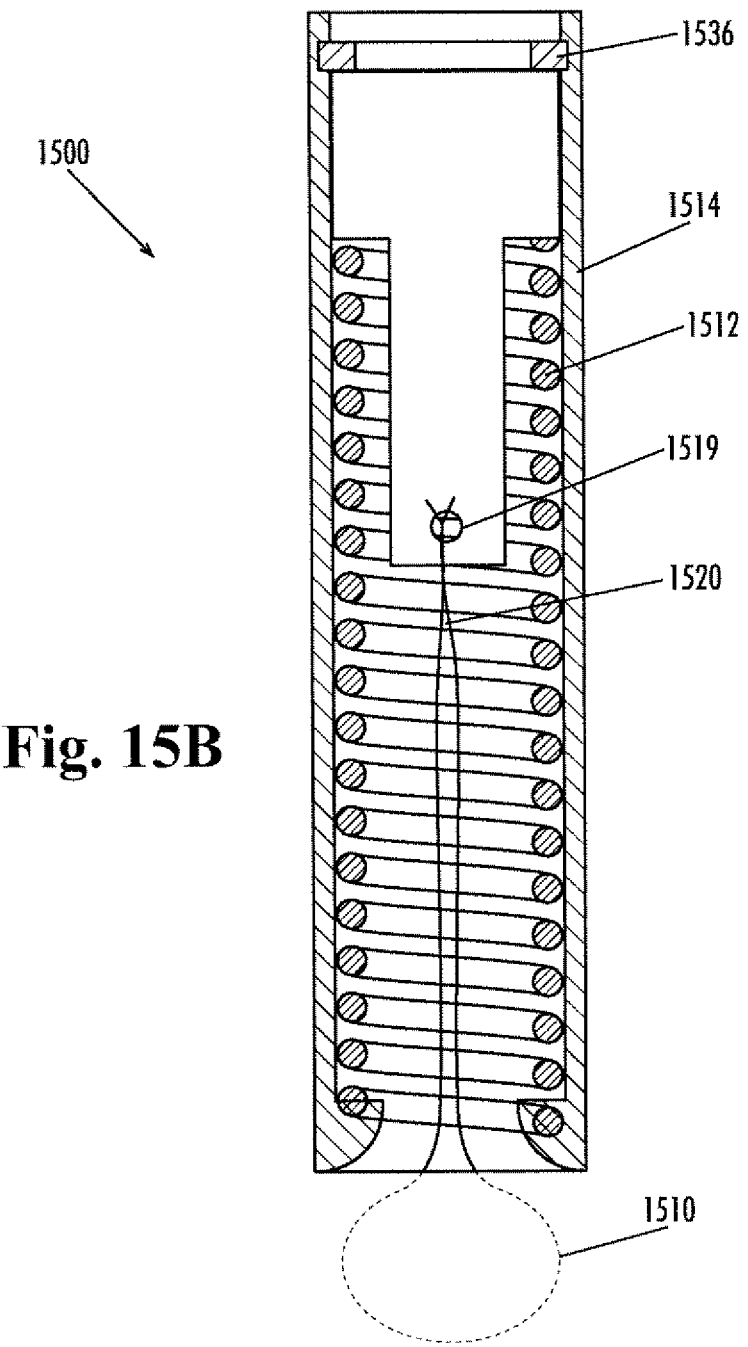
Figure 15C:
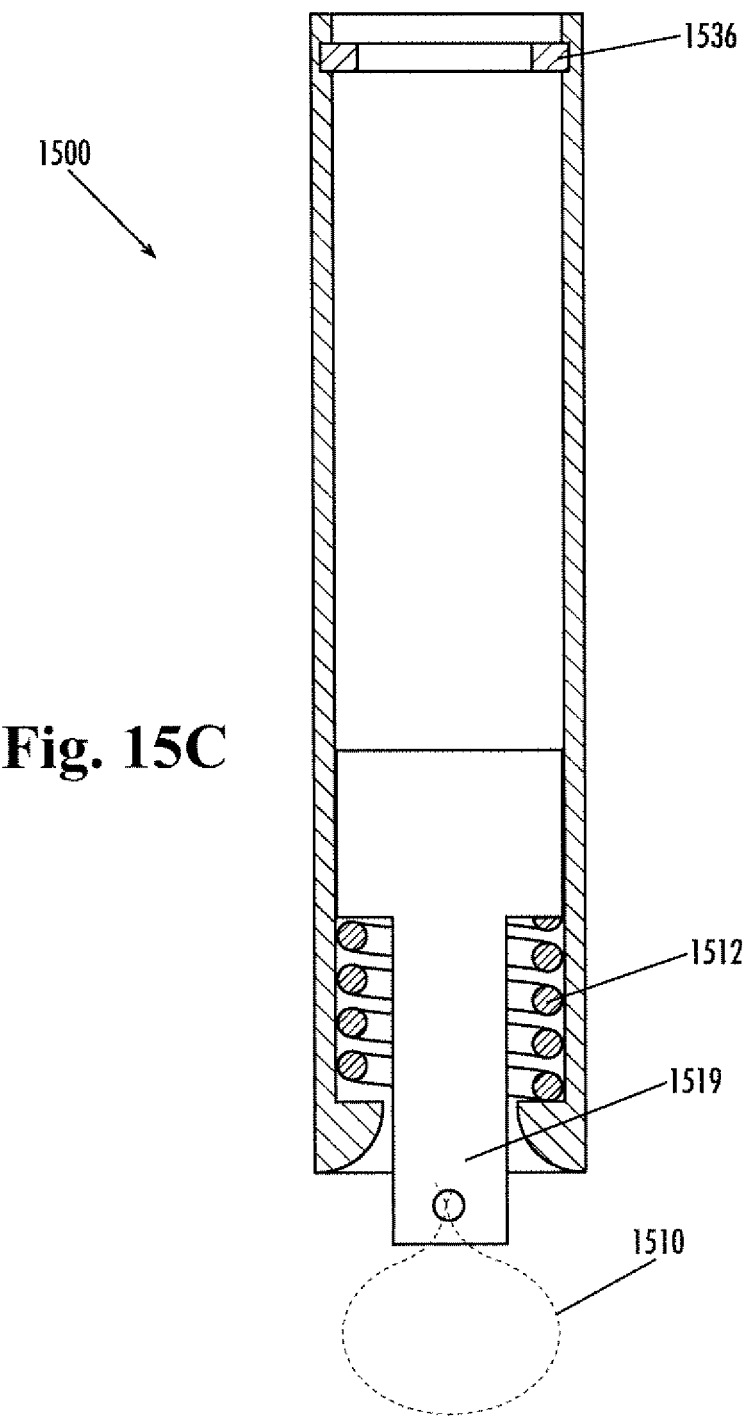

FIGS. 15A-C show another embodiment in which the tensioning element is fully encased in all states of compression and expansion. FIGS. 15A and 15B are a perspective and cross-sectional view, respectively, of the embodiment in an expanded configuration. FIG. 15C shows the embodiment in a compressed configuration. The embodiment 1500 comprises a cylindrical guide element 1514, and a tensioning element 1512, suture retaining element 1519, and stopper 1536 contained within the guide element 1514. The distal surface of the guide element 1514 contacts the tissue (not shown) 1520, and the ends of the suture 1510 are received by an opening in the distal surface and led through the passage in the guide element 1514. The passage 1520 may be the hollow channel of the guide element 1514 as a whole, as shown in FIG. 15B, or there may be a defined passage or passages within the guide element 1514, as in previous embodiments. The tensioning element 1512 expands and compresses within the guide element 1514. The distal end of the tensioning element 1512 abuts the distal inner surface of the guide element 1514, and the proximal end of tensioning element 1512 abuts the suture retaining element 1519. The suture retaining element 1519 may be attached to the proximal end of the tensioning element 1512 and slides within the guide element 1514 according to the compression and expansion of the tensioning element 1512. The stopper 1536, which can take on many forms including a snap ring, remains at the proximal end of the guide element 1514 notwithstanding movement of the other parts within the guide element 1514, as shown in FIG. 15C.

When the tensioning element 1522 expands, the proximal surface of the suture retaining element 1519 may contact the stopper 1536, at which point further expansion is blocked. The stopper 1536 also prevents the suture retaining element 1519 from exiting the guide element 1514. The length of expansion permitted within the guide element 1514 must be great enough to absorb all of the slack in the suture upon removal of the medical device. This length depends on the circumference of the suture, which in turn depends on the type of surgical procedure, circumference of the medical device, and amount of overlap in the suture within the guide element 1514.

The suture retaining element 1519 can have a variety of forms. The suture retaining element 1519 is shown to include a narrow portion which extends through the tensioning element 1512 and comprises an aperture through which the ends of the suture 1510 are tied-off, and a cylindrical portion which abuts the proximal end of the tensioning element 1512. The suture ends are tied-off through the aperture during implantation of the device 1500 while the tensioning element 1512 is compressed, as in FIG. 15C. The suture retaining element 1519 can be held in place, thereby keeping the tensioning element 1512 compressed, using a tension retaining element 1522. In one embodiment, the tension retaining element 1522 is a suture, pin, or other structure which extends through two or more holes (shown in FIG. 15A) in the guide element 1514. The suture, pin, or other structure contacts the proximal surface of the suture retaining element 1519 to block movement through the guide element 1514 and thereby holds the suture retaining element 1519 and tensioning element 1512 in place. In another embodiment, the tension retaining element 1522 extends through aligned holes in the guide element 1514 and the suture retaining element 1519. The holes in FIG. 15A are shown toward the distal end of the guide element 1514, but the holes can be located anywhere along the length of the guide element 1514. The size and shape of the holes may also vary. The tensioning element 1512 may be secured in a compressed position prior to use in a surgical procedure, in which case the tension retaining element 1522 is already in place and is removed during surgery upon implantation of the device 1500. Alternatively, the stopper 1536 can be removable to enable access to the tensioning element 1512 for compression thereof during the surgical procedure.

The embodiment shown in FIGS. 16A-E has an alternative suture retaining element. The embodiment 1600 comprises a guide element 1614, and a tensioning element 1612, suture retaining element 1619, and stopper 1636 contained within the guide element 1614. The embodiment is shown with the tensioning element 1612 compressed in FIG. 16A. The tensioning element 1612 may be held in such configuration by extending a suture retaining element (not shown) through aligned holes in the guide element 1614 (visible in FIGS. 16B-E), as discussed in the context of other embodiments.

Figure 16A:
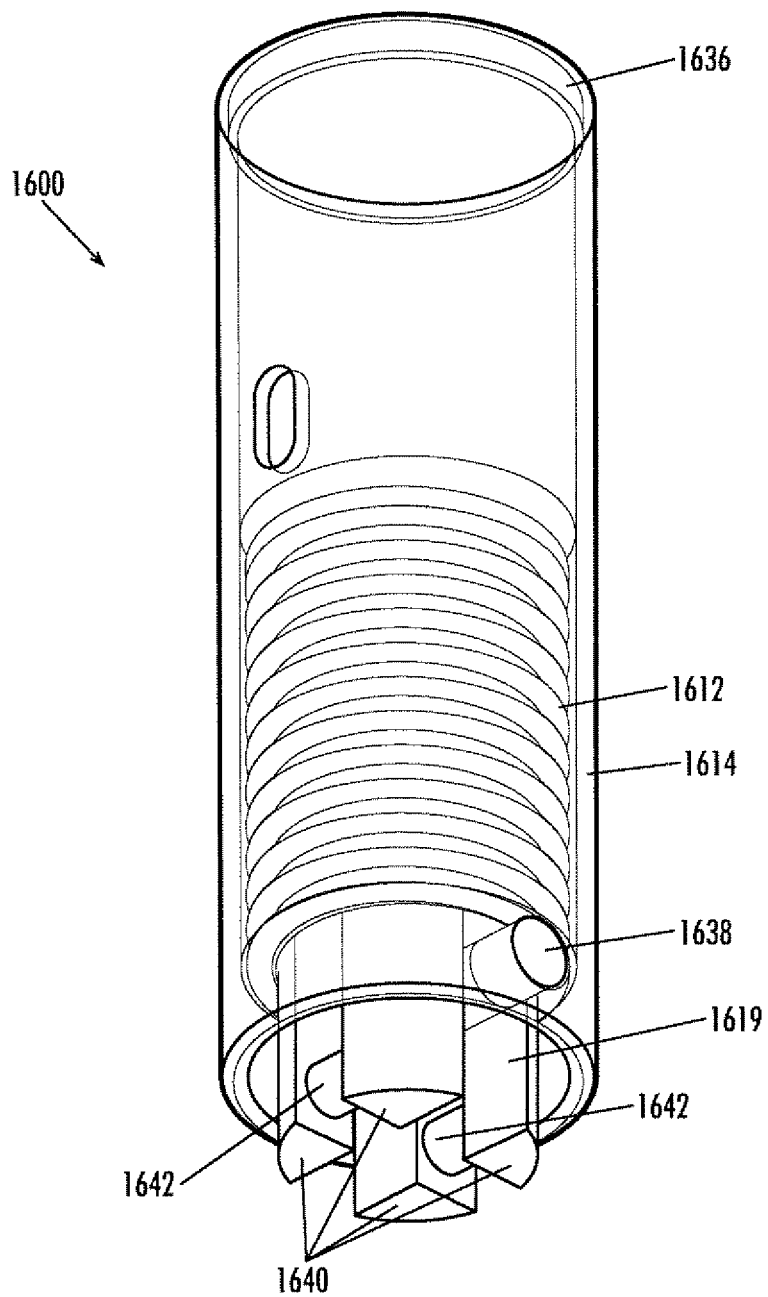
FIGS. 16A-E are views of an alternative embodiment of the purse string suture tensioning device.
Figure 16B:
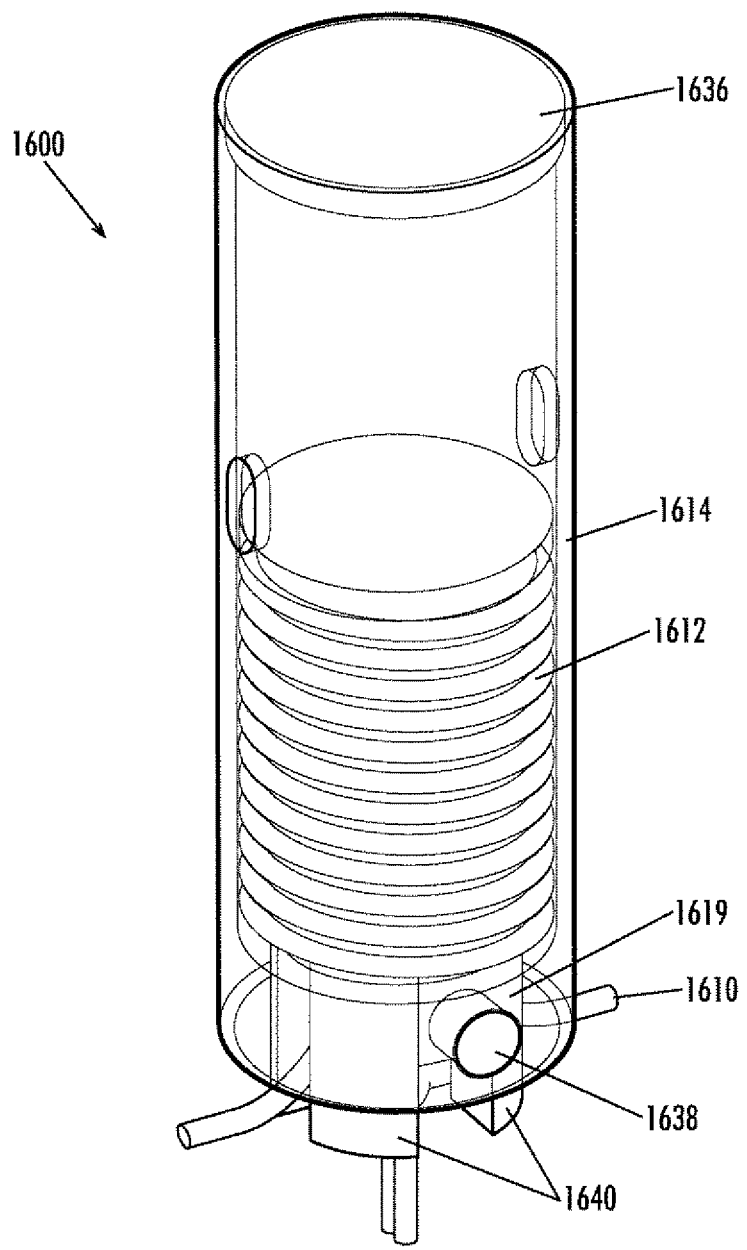
Figure 16C:
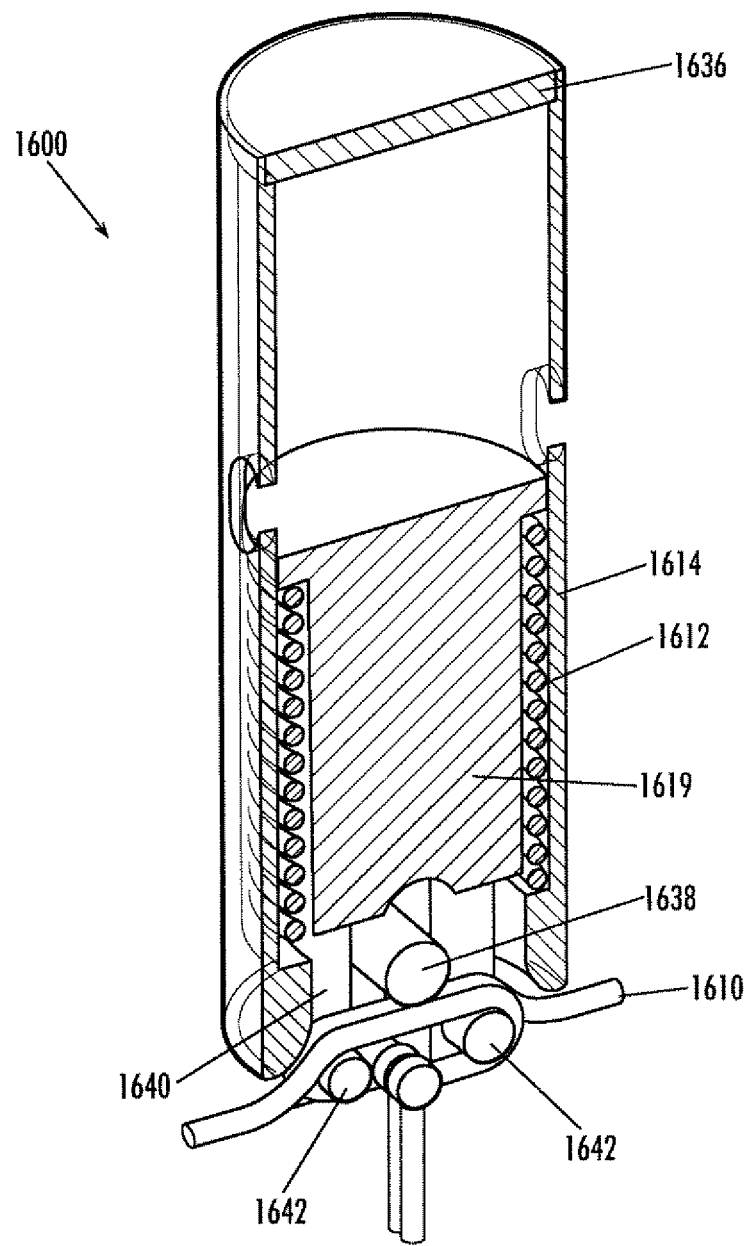

The suture retaining element 1619 comprises a cylindrical portion and four extensions 1640 therefrom. The four extensions 1640 form two pairs, and each pair has a cylindrical rod 1642 or other structure extending therebetween, as shown in FIG. 16A. The extensions 1640 reach beyond the distal end of the guide element 1614 when the tensioning element 1612 is compressed, as shown in FIG. 16A. The guide element 1614 includes a cylindrical rod 1638 or other structure extending through it near its distal end, which is used to stabilize the suture at the distal end of the guide element 1614 and facilitates greater overlap of the suture 1610, as discussed below. When the tensioning element 1612 is compressed and the extensions 1640 are thereby advanced out of the distal end of the guide element 1614, the guide element rod 1638 extends between the attached pairs of extensions 1640. During implantation, each end of the suture 1610 is threaded above the rods 1642 connecting the pairs of suture retaining element extensions 1640 and below the guide element rod 1638, as shown in FIG. 16C. The ends of the suture 1610 are then tied together beneath the extension rods 1642 or, alternatively, the suture ends may be cinched or otherwise clamped together beneath the extension rods 1642.

Figure 16D:
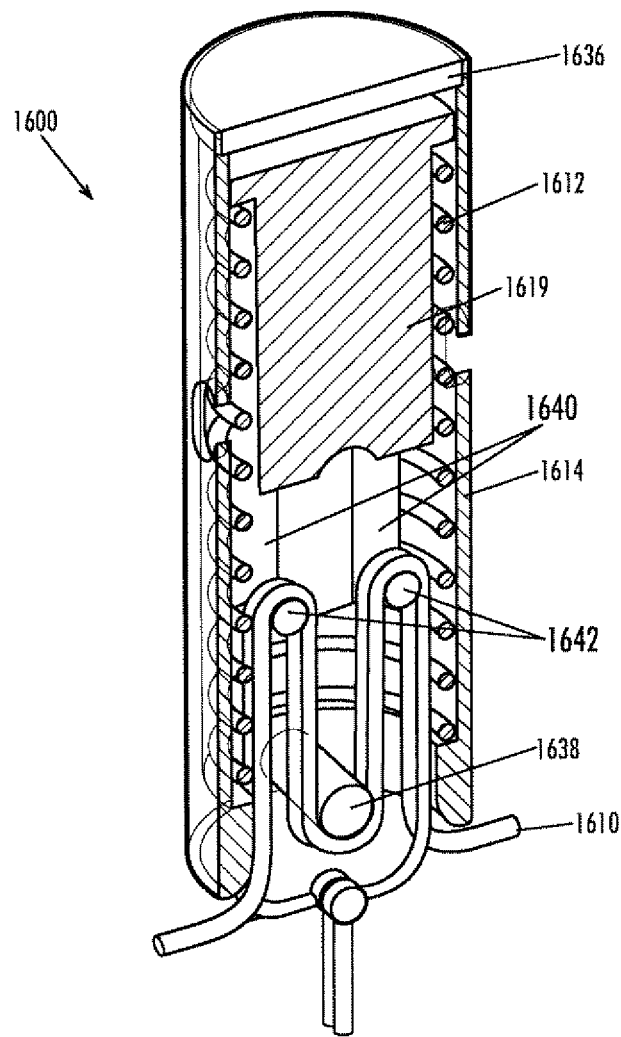
Figure 16E:
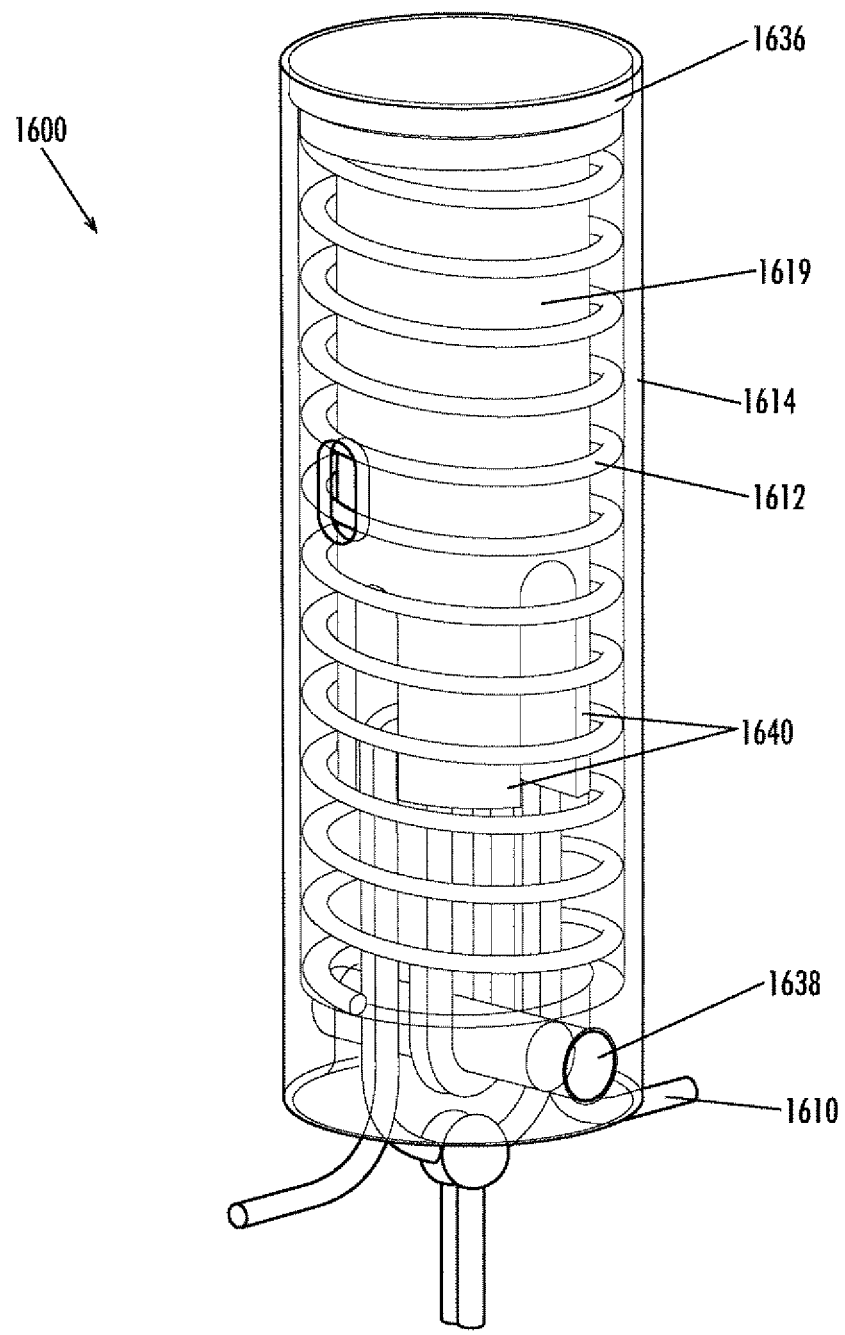

The guide element rod 1638 and the extension rods 1640 reciprocate as the tensioning element 1612 expands and compresses. The reciprocating design causes the suture 1610 to overlap within the guide element 1614 as the tensioning element 1612 expands, as shown in FIGS. 16C and 16D. This allows a greater length of slack to be absorbed within a smaller range of expansion of the tensioning element 1612 and thereby allows the guide element 1614 and the device 1600 as a whole to be made smaller.

As mentioned previously, the shape of the guide element, the orientation of the passage(s) therethrough, and position of the tensioning element(s) with respect to the guide element can vary widely. FIGS. 4-7 show various embodiments of the purse string suture tensioning device. In the embodiments shown in FIGS. 4-7, the shape of the guide element is an oval or a rectangle with rounded edges. In the tensioning device 400 in FIG. 4, the guide element 414 has a distal surface 418 adjacent the tissue 415, a proximal surface 416, and a single linear passage 420 therethrough. The device 400 also has a single tensioning element 412 proximal to the guide element 414, and a suture retaining element 419 proximal to the tensioning element 412, through which the ends of the suture 410 can be threaded and then tied-off, as shown.

Figure 5:
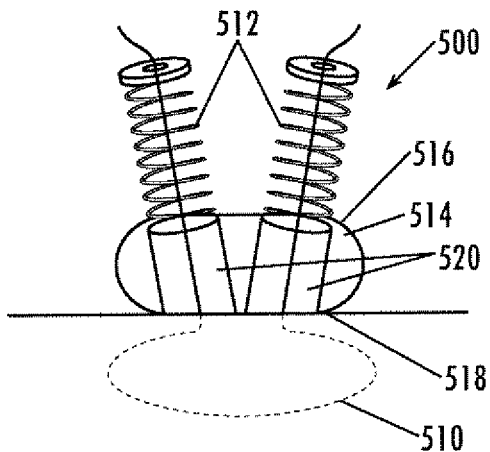
FIG. 5 is a schematic view of another embodiment of the purse string suture tensioning device.

The embodiment 500 shown in FIG. 5 comprises a guide element 514 having two passages 520, and two tensioning elements 512, with one passage 520 and one tensioning element 512 corresponding to each end of a purse string suture 510. The passages 520 are linear and extend from the distal surface 518 of the guide element 514 toward the proximal surface 516 of the guide element 514 at a slight outward diagonal. Each tensioning element 512 is located proximal to a corresponding passage 520. After the ends of the suture 510 are threaded through their respective passages 520 and tensioning elements 512, the ends of the suture 510 are either tied-off or otherwise secured proximal to the tensioning elements 512.

Figure 6:
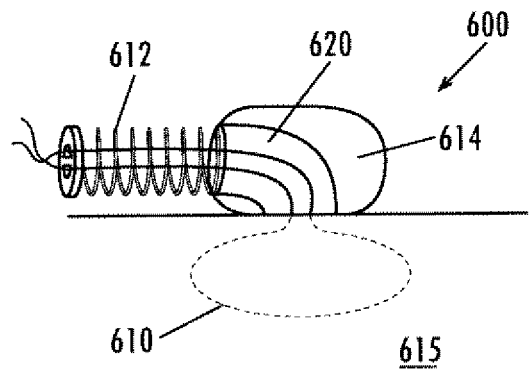
FIG. 6 is a schematic view of another embodiment of the purse string suture tensioning device.

The embodiment 600 shown in FIG. 6 has a single curved passage 620 through the guide element 614. The ends of the suture 610 enter the passage 620 approximately perpendicular to the plane of the tissue 615 and exit approximately parallel to the plane of the tissue 615. There is a single tensioning element 512 which extends from where the suture 610 exits the guide element 614 in a direction approximately parallel to the plane of the tissue 615.

The embodiment shown in FIG. 6, along with others such as that shown in FIGS. 2A-D, in which the suture ends exit the guide element passage parallel to the plane of the tissue, advantageously has a low profile. Other characteristics, such as the size and shape of the guide element, the orientation of the tensioning element to the guide element, and the type of suture retaining element, can also be chosen to obtain a low profile.

Figure 7A:
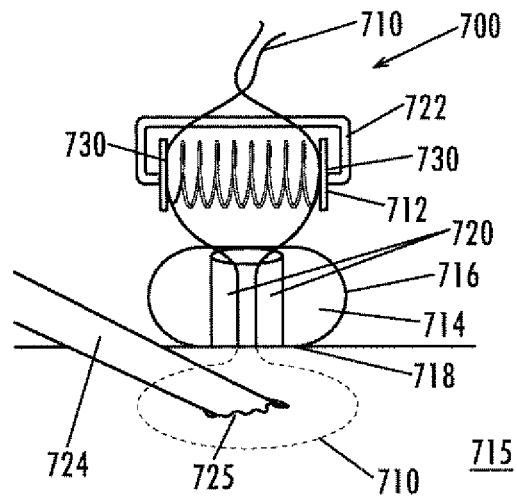
FIGS. 7A-C are schematic views of another embodiment of the purse string suture tensioning device.
Figure 7B:
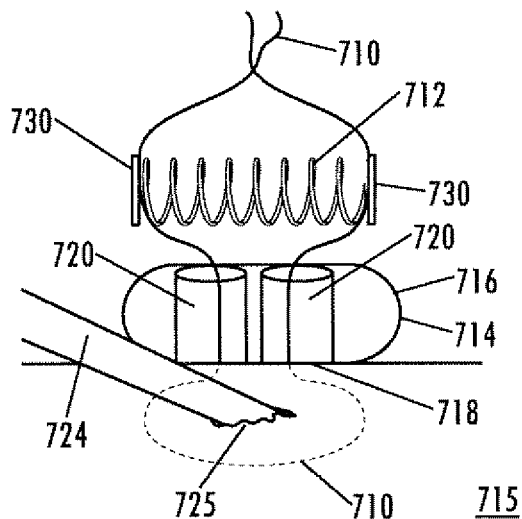
Figure 7C:
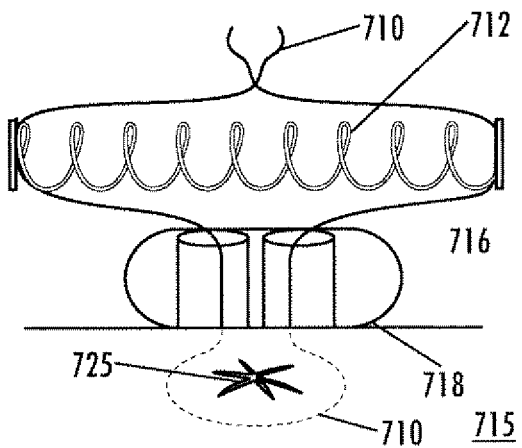

Another embodiment with a low profile is shown in FIGS. 7A-C. As shown in FIG. 7A, the tensioning device 700 includes a guide element 714 with a distal surface 718, proximal surface 716, and two passages 720 therethrough; a tensioning element 712; passage elements 730 corresponding to each end of the tensioning element 712; and a tension retaining element 722. The guide element 714 has two passages 720 therethrough, each of which is linear and substantially perpendicular to the plane of the tissue 715. The tensioning element 712 is proximal to the guide element 714 and is substantially parallel to the plane of the tissue 715. After the ends of the suture 710 are threaded through the guide element passages 720, each end is threaded through a passage element 730 corresponding to a lateral end of the tensioning element 712. Each passage element 730 may be attached to, or may be a part of, the corresponding lateral end of the tensioning element 712. In one embodiment, the passage elements 730 are bead-like structures attached to each end of the tensioning element 712. The ends of the suture 710 are not secured to the passage elements 730 because the ends must be free to slide through the passage elements 730 upon a change in compression of the tensioning element 712 in response to changes in slack in the purse string suture 710. In FIG. 7A, the device 700 is shown with the tensioning element 712 held in a compressed configuration by a tension retaining element 722 such as a C-clamp. In FIG. 7B, the tension retaining element 722 has been removed, allowing the tensioning element 712 to partially uncompress and take up the slack in the suture 710 to create hemostatis around the surgical instrument 724. FIG. 7C shows the device 700 after it has self-adjusted to create hemostasis upon removal of the surgical instrument 724 from the incision 725.

Figure 13A:
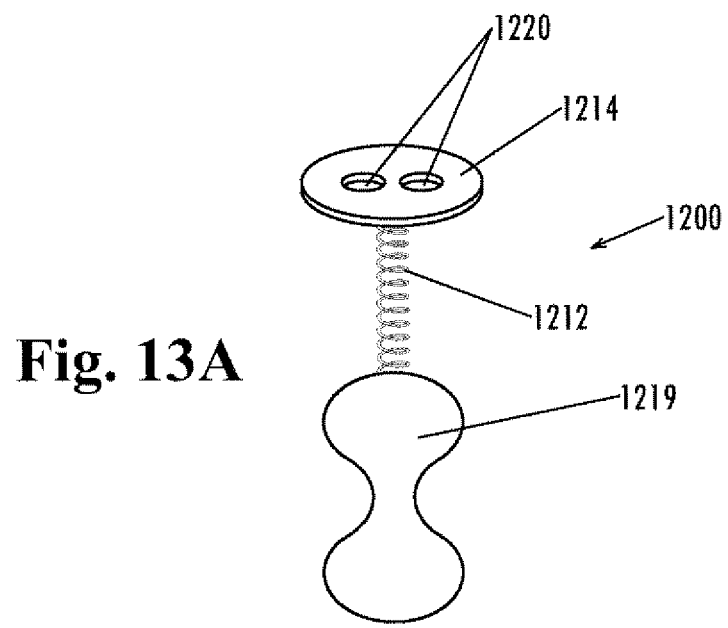
FIGS. 13A-D are schematic views of an alternative embodiment of the purse string suture tensioning device.
Figure 13B:
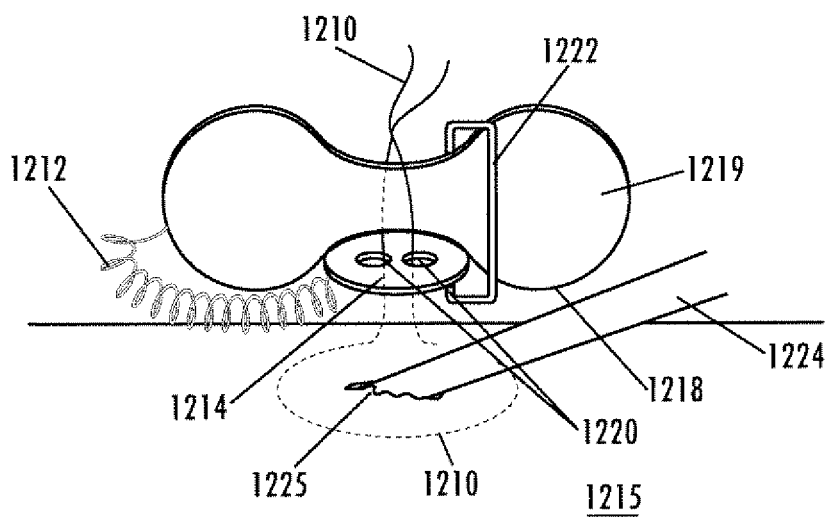
Figure 13C:
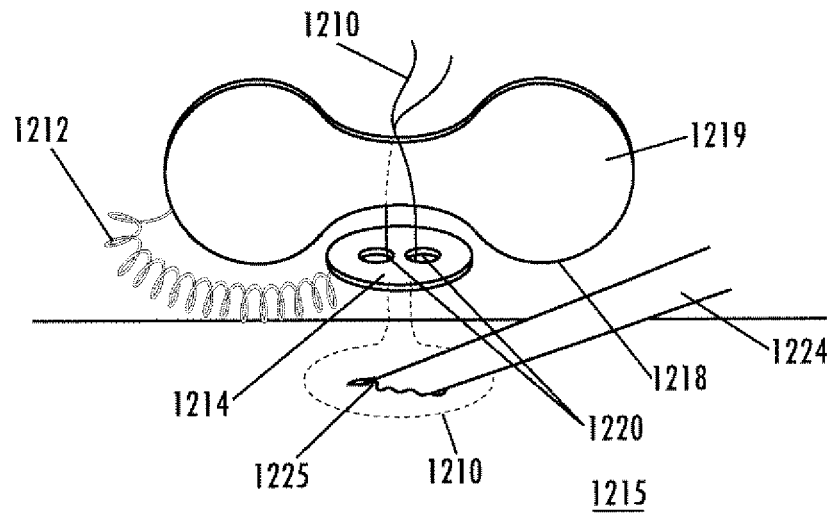
Figure 13D:
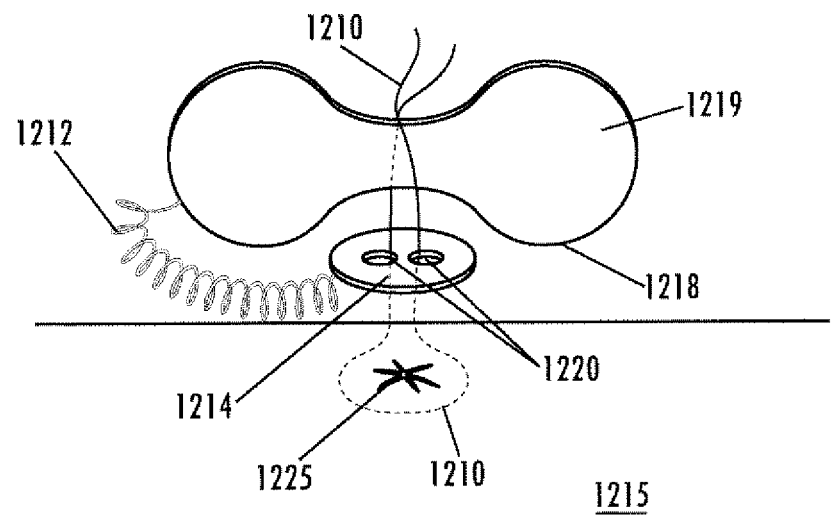

An alternative embodiment of the purse string suture tensioning device is shown in FIGS. 13A-D. The device 1200 comprises a guide element 1214 with two passages 1220, a suture retaining 1219 element around which the ends of the suture 1210 can be tied, and a tensioning element 1212 connecting the guide element 1214 to the suture retaining element 1219. The tensioning element 1212 may be covered by a protective sleeve or sheath (not shown). FIG. 13A shows the device 1200 in a relaxed configuration. FIG. 13B shows the device 1200 in operation, held in place by a tension retaining element 1222, such as a clip or clamp. The guide element 1214 is placed with the distal surface 1218 close to the tissue 1215, and the tensioning element 1212 is bent and held with the suture retaining element 1219 proximal to the guide element 1214 and such that its elongated axis is substantially parallel to the plane of the tissue 1215. The size and shape of the suture retaining element 1219 can vary widely. The suture retaining element 1219 is shown to be elongated and rounded, with two wide ends and a thin segment in the middle around which the suture ends are tied. In FIG. 13C, the tension retaining element 1222 has been removed, allowing the guide element 1214 and suture retaining element 1218 to separate slightly as the purse string suture 1210 tightens. In FIG. 13D, the surgical instrument 1224 has been removed, and the purse string 1210 has tightened around the incision 1225 as the suture retaining element 1219 separates further from the guide element 1214.

The purse string suture tensioning device can be made from any biocompatible material, including, but not limited to, stainless steel and titanium. The elements of the device can also be constructed with a variety of therapeutic coatings, such as antibiotic, antiviral or congealing compositions. Also, all or part of the purse string suture tensioning device may be covered by a biologically compatible casing. This casing can have smooth edges to lessen any irritation to the body during implantation of the tensioning device.

Figure 8:
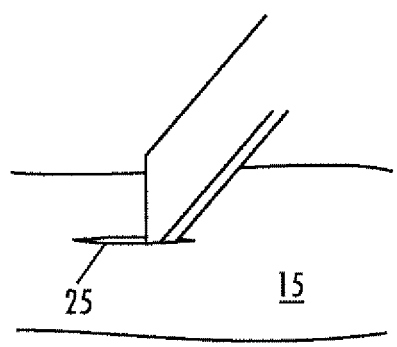
FIGS. 8-11 are a series of perspective views showing the chronology of operation of an embodiment of the purse string suture tensioning device.
Figure 9:
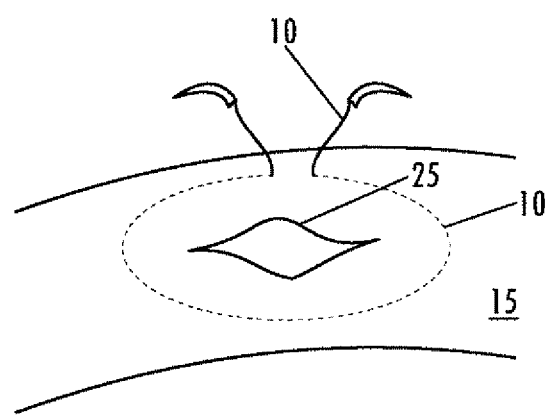
Figure 10:
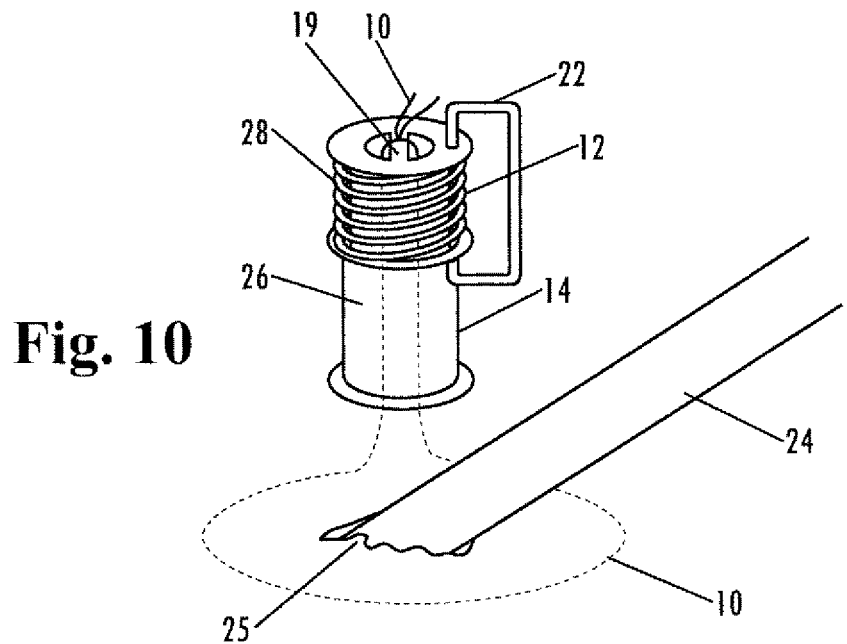

The chronology of operation of a purse string tensioning device is demonstrated in FIGS. 8-11 using the embodiment of FIG. 1. The operation of other embodiments is similar and will be understood by one skilled in the art. FIG. 8 shows a small incision 25 being made in the target tissue 15. In FIG. 9, a purse string suture 10 has been placed around the incision 25. The diameter of the purse string suture 10 should be chosen according to the size of the medical instrument to be inserted through it. Once the suture 10 is placed as a loop in the internal tissue 15 or organ, the trailing ends of the suture 10 are brought together in a purse string fashion and pulled taut (not shown). As shown in FIG. 10, the surgical instrument 24 is inserted in the incision 25. The ends of the suture 10 are then threaded through the guide element 14 and through the tensioning element 12 while it is compressed by a tension retaining element 22 such as a clamp. While the tensioning element is still compressed, the ends are tied-off around the suture retaining element 19.

Figure 11:
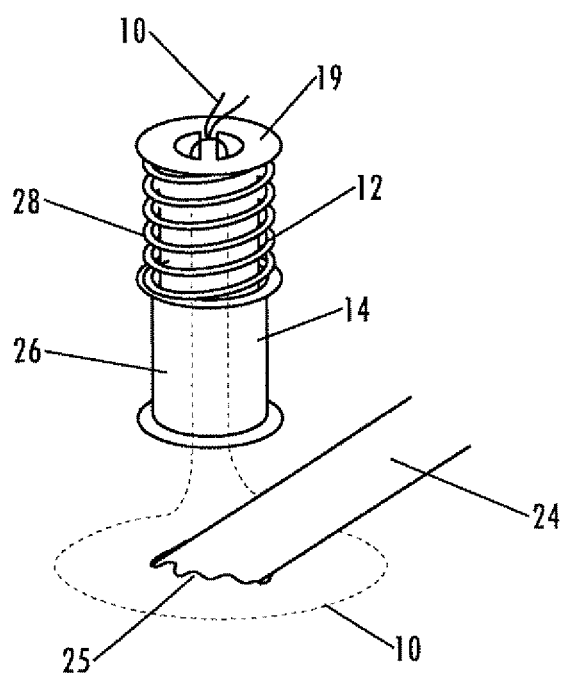

Once the suture ends are secured proximal to the compressed tensioning element 12, the tension retaining element 22 is removed, so any slack in the suture 10 is taken up by the tensioning element 12 partially uncompressing and the telescoping sections 26, 28 extending, as shown in FIG. 11. This is advantageous to compensate for any movement of the instrument 24 during the surgical procedure that causes slack. To allow further compression in case movement during the surgical procedure requires more slack, the tensioning member 12 can be not fully compressed at the point when the ends of the suture 10 are secured around the suture retaining element 19. The exact length of the suture along the compression continuum will vary according to the size of the incision, the size of the minimally invasive elongated medical device temporarily inserted into the purse string suture, and the tension desired for the particular type of tissue and condition of the patient.

Figure 12:
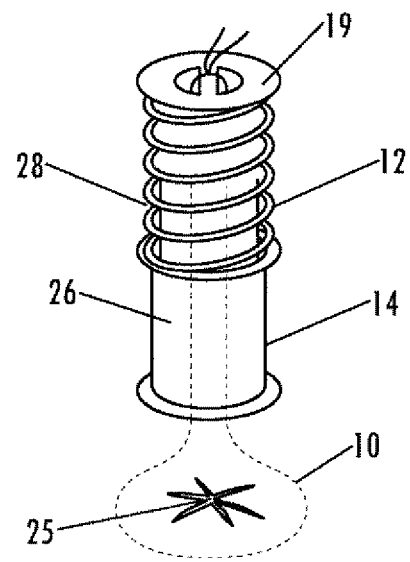
FIG. 12 is a perspective view showing the purse string tensioning device of FIG. 1 placed adjacent to the incision with the tensioning element in an uncompressed configuration upon removal of the surgical instrument through the incision.

As shown in FIG. 12, when the surgical instrument 24 is withdrawn from the incision 25, the tensioning element 12 uncompresses to tighten the suture 10 and provide a hemostatic seal without the instrument 24. Alternatively, only the outer sheath or another component of the medical instrument 24 may be withdrawn initially, leaving a guidewire, camera, or other elongated apparatus inserted. The tensioning element 12 would then uncompress partially to take up the slack upon removal of the component and to provide a seal around the remaining apparatus. When the remaining apparatus is later removed, the tensioning element 12 would uncompress further to provide a seal without any instrument or apparatus remaining in the incision.

Figure 17:
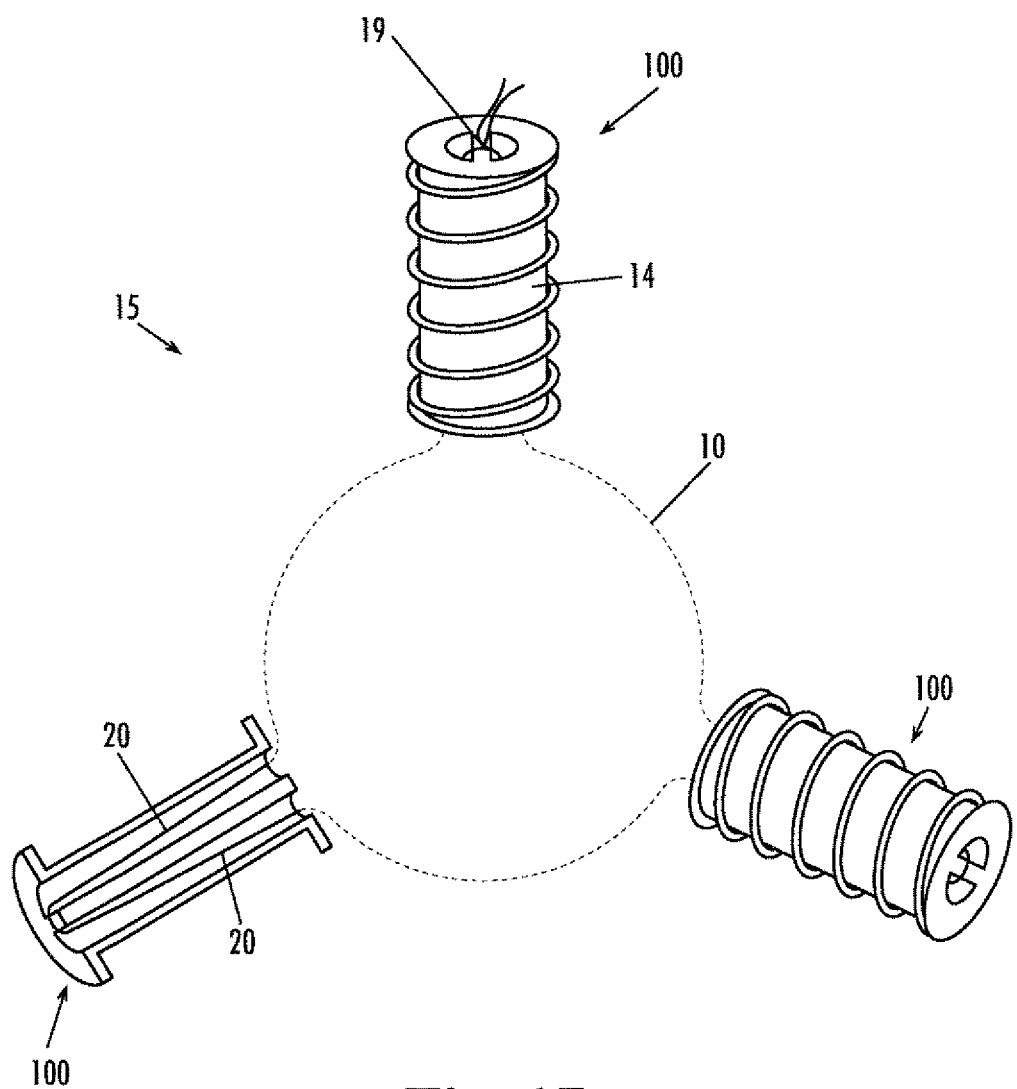
FIG. 17 is a schematic view showing multiple of one embodiment of the purse string suture tensioning device operating in series.

For larger incisions, it may be desirable to use multiple tensioning devices. As shown in FIG. 17, using the device embodiment of FIG. 1, the suture can extend through the tissue and the multiple tensioning devices in series. FIG. 17 shows a series of three devices 100, but the number of devices 100 can vary according to the surgical application. The presence of a greater number of devices 100 allows a greater length of suture slack to be taken up upon removal of the surgical instrument or due to other factors post-surgery. The ends of the purse string suture 10 are retained by the suture retaining element 17 of only the final device 100 in the series (shown as the top device in FIG. 17). For the other devices 100, the suture 10 extends away from the tissue 15 through the first passage 20 in the guide element 14, over the septum 19, and back toward the tissue 15 through the second passage 20 in the guide element (as shown in the bottom left device in FIG. 17). The suture 10 is not secured to the devices 100 at any point along its length, such that the tension on the suture 10 as a whole is altered by any one of the devices 100 taking up slack in the suture 10.

Many surgical procedures require multiple purse string sutures. For example, cannulation of the ascending aorta is typically performed with two concentric purse string sutures, given the increased potential for blood loss from that region. In the case of multiple purse string sutures, a separate tensioning device or multiple tensioning devices could be used for each suture, or a single tensioning device could be used for the multiple sutures.

What is claimed is:

1. An implantable purse string suture tensioning device comprising:
   at least one compressible tensioning element having a proximal end and a distal end;
   a suture guide element having a proximal surface and a distal surface and at least one passage therethrough for receiving a purse string suture, wherein the suture guide element comprises a plurality of telescoping elements which, when in use, permits a variable length of a suture to pass therethrough and stabilizes a suture adjacent to the tensioning element to permit absorption of excess suture length under predetermined pressure of the tensioning element to maintain tension in the suture; and
   wherein the device is sized and shaped for in-dwelling implantation in a patient.

2. The tensioning device of claim 1, wherein the passage through the guide element is linear.

3. The tensioning device of claim 1, wherein the passage through the guide element is non-linear.

4. The tensioning device of claim 1, wherein the suture is configured to enter the passage through the guide element substantially perpendicular to the plane of the tissue and exits the passage substantially parallel to the plane of the tissue.

5. The tensioning device of claim 1, wherein the guide element has two separate passages for receiving respective ends of the purse string suture.

6. The tensioning device of claim 1, wherein at least a portion of the guide element extends through the tensioning element.

7. The tensioning device of claim 1, wherein at least a portion of the tensioning element extends through the guide element.

8. The tensioning device of claim 1, further comprising a removable tension retaining element which retains the tensioning element in a compressed configuration.

9. The tensioning device of claim 1, further comprising a suture retaining element.

10. The tensioning device of claim 9, wherein the suture retaining element is a proximal septum between separate passages for each end of the purse string suture.

11. The tensioning device of claim 1, wherein the device seals a purse string suture through a range of tension required with and without an elongated medical device inserted into the purse string suture.

12. A method for sealing a purse string suture around an elongated medical device using the purse string suture tensioning device of claim 1, comprising:
- inserting at least one end of the purse string suture through the distal surface of the guide element;
- securing the at least one end of the purse string suture proximal to the tensioning element, wherein the tensioning element is in a compressed configuration while the at least one end of the purse string suture is being secured;
- releasing compression on the tensioning element to provide tension throughout the purse string; and
- closing tissue over the device.

13. The method of claim 12, wherein the compressed configuration of the tensioning element is accomplished by increasing an extent of the telescopic relationship between the telescoping elements.

14. The method of claim 12, wherein the tissue is the heart.

15. The method of claim 12, wherein the elongated medical device is a cannula.

16. The method of claim 12, wherein the tensioning element is secured in a compressed configuration by a tension retaining element, which is removed to release compression.

17. The tensioning device of claim 1, wherein one of the telescoping elements comprises a suture retaining element.

18. The tensioning device of claim 17, wherein the other telescoping element comprises a proximal guide section.

19. The tensioning device of claim 1, wherein the tensioning element comprises a spring.

20. The tensioning device of claim 1, wherein the telescoping elements comprise a distal guide section and a proximal guide section.

21. The tensioning device of claim 20, wherein the distal guide element includes a suture retaining element.

22. An implantable purse string suture tensioning device comprising:
- a guide element having a proximal surface and a distal surface and at least one passage there through, for receiving a purse string suture, wherein the suture guide element comprises a plurality of telescoping elements which, when in use, permits a variable length of a suture to pass therethrough and absorbs excess suture length under predetermined pressure to maintain tension in the suture,
- a tensioning element having a first lateral end and a second lateral end, the tensioning element applying the predetermined pressure,
- a plurality of passage elements, one attached to each end of the tensioning element, for receiving a respective end of a purse string suture;
- wherein the device is sized and shaped for in-dwelling implantation in a patient.

23. The tensioning device of claim 22, wherein the passage through the guide element is linear.

24. The tensioning device of claim 22, wherein the guide element has a plurality of passages for receiving a purse string suture.

25. The tensioning device of claim 22, further comprising a suture retaining element attached to the tensioning element, adapted for securing the ends of a purse string suture.

26. The tensioning device of claim 22, wherein the tensioning element is substantially parallel to the plane of the tissue.

27. The tensioning device of claim 22, wherein the device seals a purse string suture through a range of tension required with and without an elongated medical device inserted into the purse string suture.

28. A method for sealing a purse string suture around an elongated medical device using the purse string suture tensioning device of claim 22, comprising:
- inserting the ends of the purse string suture through the guide element;
- threading each end of the purse string suture through a corresponding passage element;
- securing the ends of the suture together, wherein the tensioning element is in a compressed configuration while the ends of the suture are being secured; and
- closing tissue over the device.

29. The method of claim 28, wherein the tissue is the heart.

30. The method of claim 28, wherein the tensioning element is secured in a compressed configuration by a tension retaining element, which is removed to release compression.

31. The method of claim 28, wherein the compressed configuration of the tensioning element is accomplished by increasing an extent of the telescopic relationship between the telescoping elements.

32. The tensioning device of claim 22, wherein one of the telescoping elements comprises a suture retaining element.

33. The tensioning device of claim 32, wherein the other telescoping element comprises a proximal guide section.

34. The tensioning device of claim 22, wherein the tensioning element comprises a spring.

35. The tensioning device of claim 22, wherein the telescoping elements comprise a distal guide section and a proximal guide section.

36. The tensioning device of claim 35, wherein the distal guide element includes a suture retaining element.

37. An implantable purse string suture tensioning device comprising:
- at least one compressible tensioning element; and
- a suture guide element having at least one passageway for receiving a purse string suture, the suture guide element comprising first and second elements arranged in spaced apart telescopic arrangement, the at least one passageway formed between the first and second elements for receiving a purse string suture of variable length, wherein the tensioning element is configured to alter an extent of the spaced apart telescopic arrangement of the first and second elements thereby absorbing excess purse string suture length under a pre-determined pressure of the tensioning element throughout changes in the purse string suture length and maintaining tension in the suture.

38. The tensioning device of claim 37, wherein one of the telescoping elements comprises a suture retaining element.

39. The tensioning device of claim 38, wherein the other telescoping element comprises a proximal guide section.

* * * * *